US008128920B2

(12) United States Patent
Sagot et al.

(10) Patent No.: US 8,128,920 B2
(45) Date of Patent: Mar. 6, 2012

(54) USE OF IL-18BP ISOFORMS FOR THE TREATMENT AND/OR PREVENTION OF NEUROLOGICAL INFLAMMATORY DISEASES

(75) Inventors: Yves Sagot, Beaumont (FR); Yolande Chvatchko, Confignon (CH); Anne Corbaz, Lausanne (CH)

(73) Assignee: Merck Serono SA, Coinsins, Vaud (CH)

( * ) Notice: Subject to any disclaimer, the term of this patent is extended or adjusted under 35 U.S.C. 154(b) by 0 days.

(21) Appl. No.: 11/915,913

(22) PCT Filed: Jun. 2, 2006

(86) PCT No.: PCT/EP2006/062864
§ 371 (c)(1),
(2), (4) Date: Nov. 29, 2007

(87) PCT Pub. No.: WO2006/128911
PCT Pub. Date: Dec. 7, 2006

(65) Prior Publication Data
US 2008/0233085 A1 Sep. 25, 2008

Related U.S. Application Data

(60) Provisional application No. 60/688,057, filed on Jun. 7, 2005.

(30) Foreign Application Priority Data

Jun. 3, 2005 (EP) .................................. 05104863

(51) Int. Cl.
*A61K 31/395* (2006.01)
*A61K 38/17* (2006.01)
*A61K 38/20* (2006.01)
(52) U.S. Cl. .................... 424/85.4; 424/134.1; 514/17.7
(58) Field of Classification Search ........................ None
See application file for complete search history.

(56) References Cited

U.S. PATENT DOCUMENTS

2002/0098185 A1* 7/2002 Sims et al. ................. 424/145.1
2003/0105057 A1 6/2003 Fu et al.

FOREIGN PATENT DOCUMENTS

| EP | 1 110 969 | | 6/2001 |
| WO | WO 99/09063 | | 2/1999 |
| WO | WO9909063 | * | 2/1999 |
| WO | WO 01/90063 | | 11/2001 |
| WO | WO 02/32374 | | 4/2002 |
| WO | WO0296456 | * | 5/2002 |
| WO | WO 2004/101617 | | 11/2004 |

OTHER PUBLICATIONS

Lazar et al Mol. Cell. Biol. 1988, vol. 8, pp. 1247-1252.*
Wells, Biochemistry, 1990, vol. 29, pp. 8509-8517.*
Halliday et al., Clin Exp Pharmacol Physiol, 2000, vol. 27, pp. 1-8.*
Steece-Collier et al., Proc Natl Acad Sci USA, 2002. vol. 99, No. 22, pp. 13972-13974.*
Feigin et al. Curr Opin Neurol, 2002, vol. 15, pp. 483-489.*
Fumagalli et al, CNS Drugs, 2008, vol. 22, No. 12, pp. 1005-1019.*
Cailleau et al, Diabetes, 1997, vol. 46, No. 6, pp. 937-940.*
Calvo et al, Pharmaceutical Research, 2001, vol. 18, No. 8, pp. 1157-1166.*
Yu et al, Journal of Neuropathology and Experimental Neurology, 2002, vol. 61, No. 7, pp. 614-622.*
Lund et al, Journal of Neurochemistry, 2005, 92, 1439-1451.*
Altschul, S. F. et al. "Basic Local Alignment Search Tool" *Journal of Molecular Biology*, 1990, pp. 403-410, vol. 215.
Altschul, S. F. et al. "Gapped BLAST and PSI-BLAST: a new generation of protein database search programs" *Nucleic Acids Research*, 1997, pp. 3389-3402, vol. 25, No. 17.
Brutlag, D. L. et al. "Improved sensitivity of biological sequence database searches" *CABIOS*, 1990, pp. 237-245, vol. 6, No. 3.
Chater, K. F. et al. "Streptomyces ØC31-Like Phages: Cloning Vectors, Genome Changes and Host Range" In *Biological, Biochemical and Biomedical Aspects of Actinomycetes*, Proceedings of the Sixth International Symposium on Actinomycetes Biology, 1985, pp. 44-53, Part A.
Comabella, M. et al. "Interferon-β treatment alters peripheral blood monocytes chemokine production in MS patients" *Journal of Neuroimmunology*, 2002, pp. 205-212, vol. 126.
Consilvio, C. et al. "Neuroinflammation, COX-2, and ALS—a dual role?" *Experimental Neurology*, 2004, pp. 1-10, vol. 187.
Conti, B. et al. "Induction of Interferon-γ Inducing Factor in the Adrenal Cortex" *Journal of Biological Chemistry*, Jan. 24, 1997, pp. 2035-2037, vol. 272, No. 4.
Conti, P. et al. "MCP-1 and Rantes Are Mediators of Acute and Chronic Inflammation" *Allergy and Asthma Proc.*, 2001, pp. 133-137, vol. 22, No. 3.
Didonato, J. A. et al. "A cytokine-responsive IκB kinase that activates the transcription factor NF-κB" Nature, Aug. 7, 1997, pp. 548-554, vol. 388.
Eikelenboom, P. et al. "Neuroinflammation in Alzheimer's Disease and Prion Disease" *GLIA*, 2002, pp. 232-239, vol. 40.
Gao, H.-W. et al. "Novel anti-inflammatory therapy for Parkinson's disease" *TRENDS in Pharmacological Sciences*, Aug. 2003, pp. 395-401, vol. 24, No. 8.
Gonnet, G. H. et al. "Exhaustive Matching of the Entire Protein Sequence Database" *Science*, Jun. 5, 1992, pp. 1443-1445, vol. 256.
Grantham, R. "Amino Acid Difference Formula to Help Explain Protein Evolution" *Science*, Sep. 6, 1974, pp. 862-864, vol. 185, No. 4154.
Henikoff, S. et al. "Performance Evaluation of Amino Acid Substitution Matrices" *PROTEINS: Structure, Function, and Genetics*, 1993, pp. 49-61, vol. 17.
Hua, L. L. et al. "Modulation of astrocyte inducible nitric oxide synthase and cytokine expression by interferon β is associated with induction and inhibition of interferon γ-activated sequence binding activity" *Journal of Neurochemistry*, 2002, pp. 1120-1128, vol. 83.

(Continued)

*Primary Examiner* — Jeffrey Stucker
*Assistant Examiner* — Fozia Hamud
(74) *Attorney, Agent, or Firm* — Saliwanchik, Lloyd & Eisenschenk

(57) ABSTRACT

The invention relates to the use of an IL18-BP isoform that does not bind to IL18, or of an agonist thereof, for treatment or prevention of a neurological and/or inflammatory disease. Preferred isoforms for use in the frame of the invention include IL-18BPb and IL-18BPd.

24 Claims, 9 Drawing Sheets

OTHER PUBLICATIONS

Infante, J. et al. "Interleukin-8, intercellular adhesion molecule-1 and tumour necrosis factor-α gene polymorphisms and the risk for multiple system atrophy" *Journal of the Neurological Sciences*, 2005, pp. 11-13, vol. 228.

Karlin, S. et al. "Methods for assessing the statistical significance of molecular sequence features by using general scoring schemes" *Proc. Natl. Acad. Sci. USA*, Mar. 1990, pp. 2264-2268, vol. 87.

Kim, S.-H. et al. "Structural requirements of six naturally occurring isoforms of the IL-18 binding protein to inhibit IL-18" *PNAS*, Feb. 1, 2000, pp. 1190-1195, vol. 97, No. 3.

Maliszewski, C. R. et al. "Cytokine Receptors and B Cell Functions I. Recombinant Soluble Receptors Specifically Inhibit IL-1- and IL-4 Induced B Cell Activities In Vitro" *Journal of Immunology*, Apr. 15, 1990, pp. 3028-3033, vol. 144.

Mallat, Z. et al. "Evidence for altered interleukin (IL)-18 pathway in human heart failure" *FASEB Journal*, Sep. 15, 2004, pp. 1-19, No. 10.1096.

Micallef, M. J. et al. "Interferon-γ-inducing factor enhances T helper 1 cytokine production by stimulated human T cells: synergism with interleukin-12 for interferon-γ production" *European Journal of Immunology*, 1996, pp. 1647-1651, vol. 26.

Nakamura, K. et al. "Endotoxin-Induced Serum Factor That Stimulates Gamma Interferon Production" *Infection and Immunity*, Feb. 1989, pp. 590-595, vol. 57, No. 2.

Noseworthy, J. H. "Progress in determining the causes and treatment of multiple sclerosis" *Nature*, Jun. 24, 1999, pp. A40-A47, vol. 399.

Novick, D. et al. "Interleukin-18 Binding Protein: A Novel Modulator of the Th1 Cytokine Response" *Immunity*, Jan. 1999, pp. 127-136, vol. 10.

Panenka, W. et al. "P2X7-Like Receptor Activation in Astrocytes Increases Chemokine Monocyte Chemoattractant Protein-1 Expression via Mitogen-Activated Protein Kinase" *Journal of Neuroscience*, Sep. 15, 2001, pp. 7135-7142, vol. 21, No. 18.

Parnet, P. et al. "IL-1Rrp Is a Novel Receptor-like Molecule Similar to the Type I Interleukin-1 Receptor and its Homologues T1/ST2 and IL-1R AcP" *Journal of Biological Chemistry*, Feb. 23, 1996, pp. 3967-3970, vol. 271, No. 8.

Pearson, W. R. et al. "Improved tools for biological sequence comparison" *Proc. Natl. Acad. Sci. USA*, Apr. 1988, pp. 2444-2448, vol. 85.

Perry, V. H. "The influence of systemic inflammation on inflammation in the brain: implications for chronic neurodegenerative disease" *Brain, Behavior, and Immunity*, 2004, pp. 407-413, vol. 18.

Pfitzner, E. et al. "The Role of STATs in Inflammation and Inflammatory Diseases" *Current Pharmaceutical Design*, 2004, pp. 2839-2850, vol. 10.

Rothe, H. et al. "Active Stage of Autoimmune Diabetes is Associated with the Expression of a Novel Cytokine, IGIF, Which Is Located Near *Idd2*" *Journal of Clinical Investigation*, Feb. 1997, pp. 469-474, vol. 99, No. 3.

Stoll, G. et al. "Degeneration and regeneration of the peripheral nervous system: From Augustus Waller's observations to neuroinflammation" *Journal of the Peripheral Nervous System*, 2002, pp. 13-27, vol. 7.

Thompson, J. D. et al. "Clustal W: improving the sensitivity of progressive multiple sequence alignment through sequence weighting, position-specific gap penalties and weight matrix choice" *Nucleic Acids Research*, 1994, pp. 4673-4680, vol. 22, No. 22.

Tuppo, E. E. et al. "The role of inflammation in Alzheimer's disease" *International Journal of Biochemistry & Cell Biology*, 2005, pp. 289-305, vol. 37.

Ushio, S. et al. "Cloning of the cDNA for Human IFN-γ-Inducing Factor, Expression in *Escherichia coli*, and Studies on the Biologic Activities of the Protein" *Journal of Immunology*, 1996, pp. 4274-4279, vol. 156.

Yan, R. et al. "The genomic structure of the STAT genes: multiple exons in coincident sites in Stat1 and Stat2" *Nucleic Acids Research*, 1995, pp. 459-463, vol. 23, No. 3.

Yatsiv, I. et al. "Elevated Intracranial IL-18 in Humans and Mice After Traumatic Brain Injury and Evidence of Neuroprotective Effects of IL-18—Binding Protein After Experimental Closed Head Injury" *Journal of Cerebral Blood Flow & Metabolism*, 2002, pp. 971-978, vol. 22.

Yoshimoto, T. et al. "IL-12 Up-Regulates IL-18 Receptor Expression on T Cells, Th1 Cells, and B Cells: Synergism with IL-18 for IFN-γ Production" *Journal of Immunology*, 1998, pp. 3400-3407, vol. 161.

Higgins, D.G. et al. "Using CLUSTAL for Multiple Sequence Alignments" *Methods in Enzymology*, 1996, pp. 383-402, vol. 266.

* cited by examiner

Figure 2

```
IL-18BPa    TPVSQTTTAA TASVRSTKDP CPSQPPVFPA AKQCPALEVT WPEVEVPL
IL-18BPc    TPVSQTTTAA TASVRSTKDP CPSQPPVFPA AKQCPALEVT WPEVEVPL
IL-18BPd    TPVSQTTTAA TASVRSTKDP CPSQPPVFPA AKQCPALEVT WPEVEVPL
IL-18BPb    TPVSQTTTAA TASVRSTKDP CPSQPPVFPA AKQCPALEVT WPEVEVPL

IL-18BPa    NGTLSLSCVACS RFPNFSILYW LGNGSFIEHL PGRLWEGSTS RERGSTG
IL-18BPc    NGTLSLSCVACS RFPNFSILYW LGNGSFIEHL PGRLWEGSTS RERGSTG
IL-18BPd    NGTLSLSCVACS RFPNFSILYW LGNGSFIEHL PGRLWEGSTS RERGSTG
IL-18BPb    ---------- ---------- ---------- ---------- -------

IL-18BPa    TQLCKALVLEQLT PALHSTNFSC VLVDPEQVVQ RHVVLAQLW
IL-18BPc    TQLCKALVLEQLT PALHSTNFSC VLVDPEQVVQ RHVVLAQLW
IL-18BPd    ---------- ---------- ---------- ---------
IL-18BPb    ---------- ---------- ---------- ---------

IL-18BPa    AGLRATLPPT QEALPSSHSS PQQQG
IL-18BPc    VRSPRRGLQE QEELCFHMWG GKGGLCQSSL
IL-18BPd    -WAEGNLAPH PRSPALQPQQ STAAGLRLST GPAAAQP
IL-18BPb    SWAEGNLAPH PRSPALQPQQ STAAGLRLST GPAAAQP
```

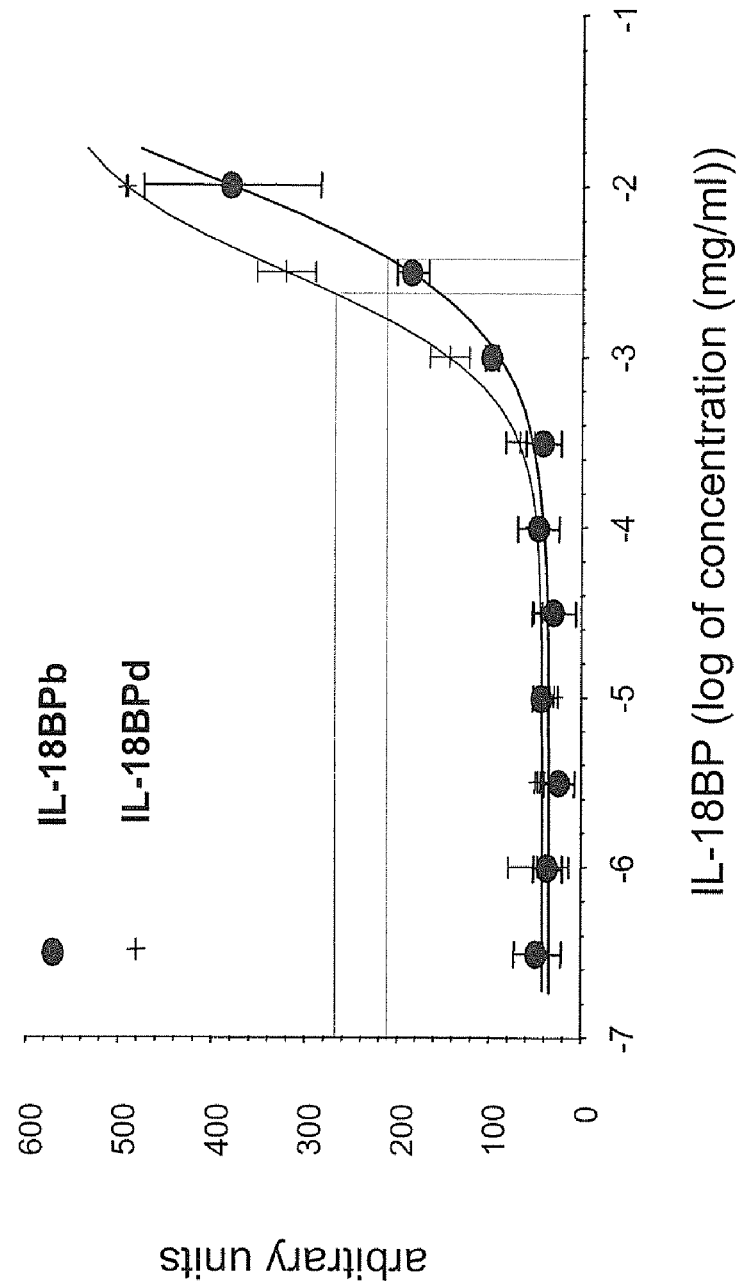

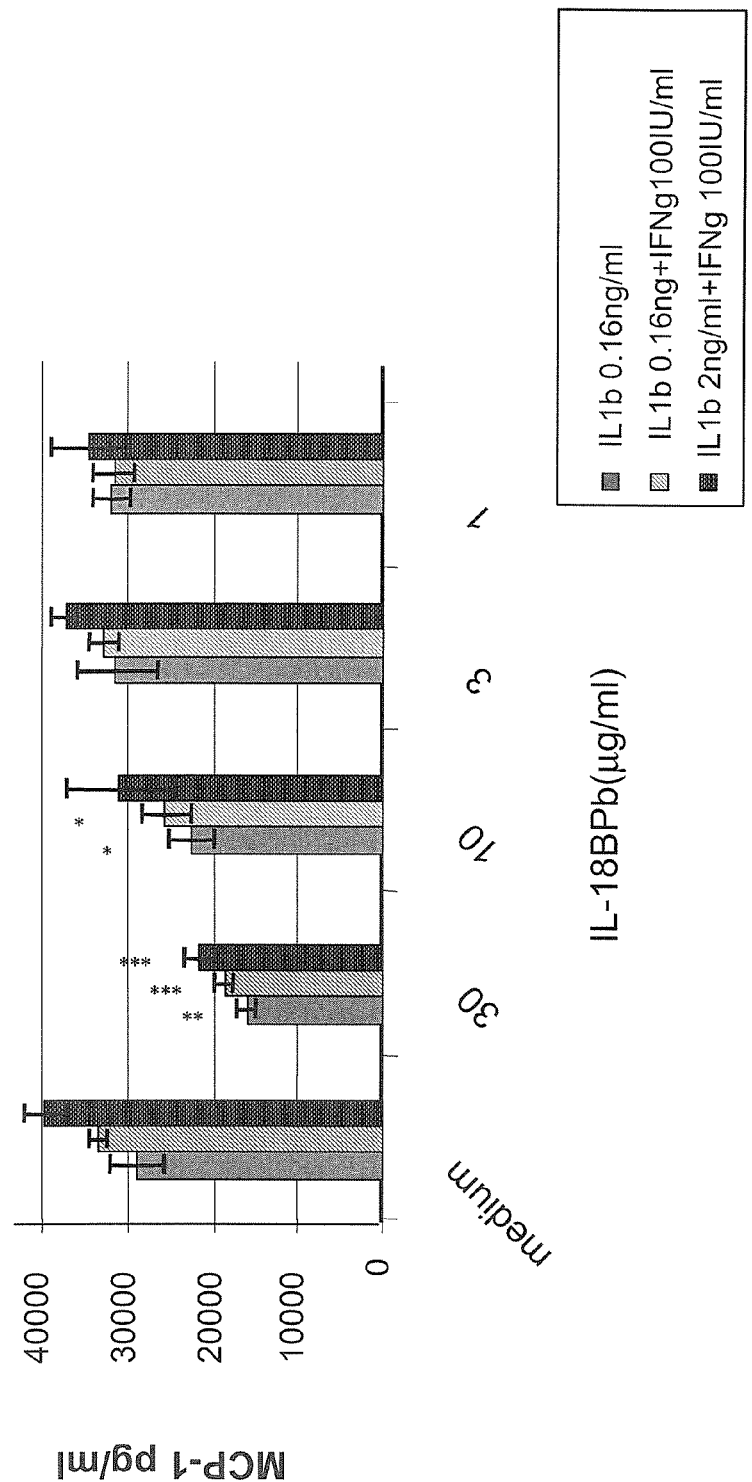

USE OF IL-18BP ISOFORMS FOR THE TREATMENT AND/OR PREVENTION OF NEUROLOGICAL INFLAMMATORY DISEASES

CROSS-REFERENCE TO RELATED APPLICATION

This application is the U.S. national stage application of International Patent Application No. PCT/EP2006/062864, filed Jun. 2, 2006, which claims the benefit of U.S. Provisional Patent Application No. 60/688,057, filed Jun. 7, 2005, the disclosures of which are hereby incorporated by reference in their entireties, including all figures, tables and amino acid or nucleic acid sequences.

FIELD OF THE INVENTION

The present invention is generally in the field of neurological diseases associated with neuro-inflammation. More specifically, the present invention relates to the use of IL-18BP isoforms that do not bind to IL-18, such as IL-18BPb and IL-18BPd, for the manufacture of a medicament for treatment and/or prevention of a neurological and/or inflammatory disease.

BACKGROUND OF THE INVENTION

1. Neurological Diseases Associated with Neuro-Inflammation.

Neuro-inflammation is a common feature to most neurological diseases. Many stimuli are triggering neuro-inflammation, which can either be induced by neuronal or oligodendroglial suffering, or be a consequence of a trauma, of a central or peripheral nerve damage or of a viral or bacterial infection. The main consequences of neuro-inflammation are (i) secretion of various inflammatory chemokines by astrocytes; and (ii) recruitment of additional leukocytes, which will further stimulate astrocytes. In chronic neurodegenerative diseases such as multiple sclerosis (MS), Alzheimer disease (AD) or amyotrophic lateral sclerosis (ALS), the presence of persistent neuro-inflammation is though to participate to the progression of the disease. Neurological diseases associated with neuro-inflammation can also be referred to as neurological inflammatory diseases.

Chronic Neurodegenerative Diseases

In chronic neurodegenerative diseases, the pathology is associated with an inflammatory response. Recent evidence suggests that systemic inflammation may impact on local inflammation in the diseased brain leading to exaggerated synthesis of inflammatory cytokines and other mediators in the brain, which may in turn influence behavior (Perry, 2004). Chronic neurodegenerative diseases comprise, among others, multiple sclerosis (MS), Alzheimer's disease (AD), Parkinson's disease (PD), Huntington's disease (HD), amyotrophic lateral sclerosis (ALS), multiple system atrophy (MSA), prion disease and Down Syndrome.

Alzheimer's disease (AD) is a disorder involving deterioration in mental functions resulting from changes in brain tissue. This includes shrinking of brain tissues, not caused by disorders of the blood vessels, primary degenerative dementia and diffuse brain atrophy. Alzheimer's disease is also called senile dementia/Alzheimer's type (SDAT). Considerable evidence gained over the past decade has supported the conclusion that neuroinflammation is associated with Alzheimer's disease (AD) pathology (Tuppo and Arias, 2005). It is the most common cause of intellectual decline with aging. The incidence is approximately 9 out of 10,000 people. This disorder affects women slightly more often than men and occurs primarily in older individuals. The cause is unknown. The neurochemical factors which may participate in generation of the disease include lack of the substances used by the nerve cells to transmit nerve impulses (neurotransmitters), including acetylcholine, somatostatin, substance P, and norepinephrine. Environmental factors include exposure to aluminum, manganese, and other substances. The infectious factors include prion (virus-like organisms) infections that affect the brain and spinal cord (central nervous system). In some families (representing 5 to 10% of cases) there is an inherited predisposition to development of the disorder, but this does not follow strict (Mendelian) patterns of inheritance. The diagnosis is usually made by ruling out other causes of dementia. The onset is characterized by impaired memory, with progressive loss of intellectual function. There may be mood changes, changes in language capability, changes in gait, and other changes as the disorder progresses. There is a decrease in the size (atrophy) of the tissues of the brain, enlargement of the ventricles (the spaces within the brain), and deposits within the tissues of the brain.

Parkinson's disease (PD) is a disorder of the brain characterized by shaking and difficulty with walking, movement, and coordination. The disease is associated with damage to a part of the brain that controls muscle movement. It is also called paralysis agitans or shaking palsy. Increasing evidence from human and animal studies has suggested that neuroinflammation is an important contributor to the neuronal loss in PD (Gao et al., 2003). The disease affects approximately 2 out of 1,000 people, and most often develops after age 50. It affects both men and women and is one of the most common neurological inflammatory diseases of the elderly. The term "parkinsonism" refers to any condition that involves a combination of the types of changes in movement seen in Parkinson's disease, which happens to be the most common condition causing this group of symptoms. Parkinsonism may be caused by other disorders or by external factors (secondary parkinsonism). Parkinson's disease is caused by progressive deterioration of the nerve cells of the part of the brain that controls muscle movement (the basal ganglia and the extrapyramidal area). Dopamine, which is one of the substances used by cells to transmit impulses (transmitters), is normally produced in this area. Deterioration of this area of the brain reduces the amount of dopamine available to the body. Insufficient dopamine disturbs the balance between dopamine and other transmitters, such as acetylcholine. Without dopamine, the nerve cells cannot properly transmit messages, and this results in the loss of muscle function. The exact reason that the cells of the brain deteriorate is unknown. The disorder may affect one or both sides of the body, with varying degrees of loss of function. In addition to the loss of muscle control, some people with Parkinson's disease become severely depressed. Although early loss of mental capacities is uncommon, with severe Parkinson's the person may exhibit overall mental deterioration (including dementia, hallucinations, and so on). Dementia can also be a side effect of some of the medications used to treat the disorder.

Huntington's Disease (HD) is an inherited, autosomal dominant neurological inflammatory disease. The disease does not usually become clinically apparent until the fifth decade of life, and results in psychiatric disturbance, involuntary movement disorder, and cognitive decline associated with inexorable progression to death, typically 17 years following onset. The gene responsible for Huntington's disease is called huntingtin. It is located on chromosome 4p, presenting an effective means of preclinical and antenatal diagnosis.

The genetic abnormality consists in an excess number of tandemly repeated CAG nucleotide sequences. Other diseases with CAG repeats include, for example, spinal muscular atrophies (SMA), such as Kennedy's disease, and most of the autosomal dominant cerebellar ataxias (ADCAs) that are known as spinocerebellar ataxias (SCAs) in genetic nomenclature. In HD, it is not known how this widely expressed gene, results in selective neuronal death. Further, sequence analysis revealed no obvious homology to other known genes and no structural motifs or functional domains were identified which clearly provide insights into its function. In particular, the question of how these widely expressed genes cause selective neuronal death remains unanswered.

Amyotrophic Lateral Sclerosis (ALS) is a disorder causing progressive loss of nervous control of voluntary muscles because of destruction of nerve cells in the brain and spinal cord. Amyotrophic Lateral Sclerosis, also called Lou Gehrig's disease, is a disorder involving loss of the use and control of muscles. The nerves controlling these muscles shrink and disappear, which results in loss of muscle tissue due to the lack of nervous stimulation. Although the root cause of ALS remains unknown, neuroinflammation may play a key role in ALS (Consilvio et al., 2004). Muscle strength and coordination decreases, beginning with the voluntary muscles (those under conscious control, such as the muscles of the arms and legs). The extent of loss of muscle control continues to progress, and more and more muscle groups become involved. There may be a loss of nervous stimulation to semi-voluntary muscles, such as the muscles that control breathing and swallowing. There is no effect on ability to think or reason. The cause is unknown. ALS affects approximately 1 out of 100,000 people. It appears in some cases to run in families. The disorder affects men more often than women. Symptoms usually do not develop until adulthood, often not until after age 50.

Multiple system atrophy (MSA) is a sporadic, adult-onset neurodegenerative disease of unknown etiology. The condition may be unique among chronic neurodegenerative diseases by the prominent, if not primary, role played by the oligodendroglial cell in the pathogenetic process. Data support a role for inflammation-related genes in risk for MSA (Infante et al., 2005). The major difference to Parkinson's disease is that MSA patients do not respond to L-dopa treatment.

Multiple sclerosis (MS) is an inflammatory demyelinating disease of the central nervous system (CNS) that takes a relapsing-remitting or a progressive course. MS is not the only demyelinating disease. Its counterpart in the peripheral nervous system (PNS) is chronic inflammatory demyelinating polyradiculoneuropathy (CIDP). In addition, there are acute, monophasic disorders, such as the inflammatory demyelinating polyradiculoneuropathy termed Guillain-Barré syndrome (GBS) in the PNS, and acute disseminated encephalomyelitis (ADEM) in the CNS. Both MS and GBS are heterogeneous syndromes. In MS different exogenous assaults together with genetic factors can result in a disease course that finally fulfils the diagnostic criteria. In both diseases, axonal damage can add to a primarily demyelinating lesion and cause permanent neurological deficits. MS is an autoimmune disorder in which leukocytes of the immune system launch an attack on the white matter of the central nervous system (CNS). The gray matter may also be involved. Although the precise etiology of MS is not known, contributing factors may include genetic, bacterial and viral infection. In its classic manifestation (85% of all cases), it is characterized by alternating relapsing/remitting phases, which correspond to episodes of neurological dysfunction lasting several weeks followed by substantial or complete recovery (Noseworthy, 1999). Periods of remission grow shorter over time. Many patients then enter a final disease phase characterized by gradual loss of neurological function with partial or no recovery. This is termed secondary progressive MS. A small proportion (~15% of all MS patients) suffers a gradual and uninterrupted decline in neurological function following onset of the disease (primary progressive MS). Molecular mechanisms underlying MS pathogenesis appear to stem from genetic and environmental factors, including viral and bacterial infections. These mechanisms promote increased migration of T lymphocytes and macrophages across the blood-brain barrier and into CNS tissue. Genetic and environmental elements lead to an increased influx of inflammatory cells across the blood-brain barrier. This results in the increased migration of autoreactive T lymphocytes and macrophages into CNS tissue. Cytokine secretion by T cells activates antigen-presenting cells (APCs). When autoreactive T cells in the context of MHC class II molecules on APCs encounter putative 'MS antigens', often protein constituents of the myelin sheath, they may become activated. Several subsequent mechanisms can then act to damage oligodendrocytes and myelin. Complement- and antibody-mediated cytotoxicity may cause the majority of damage in some patients, while Fas-ligand signaling, and release of pro-inflammatory cytokines like TNF-a by CD4+ T cells may attack white matter in others. Activated macrophages may also play a role through enhanced phagocytosis and factor secretion. This causes widespread demyelination and subsequent loss of conduction efficiency among the axons of the CNS. Subsequent repair mechanisms can, however, give rise to remyelination once the inflammatory process is resolved. The remyelinated axons of MS patients are recognized pathologically by the thin appearance of the sheaths around the remyelinated axons. Additional sodium channels and an abnormal repertoire of ions channels, are often found inserted into the demyelinated axonal membrane, trying to compensate for the loss of conduction efficiency. These aberrant patterns of expression suggest that MS may also include a channelopathy. Oligodendroglial precursors may enhance remyelination in MS lesions.

Prion disease and Down Syndrome have also been shown to involve neuroinflammation (Eikelenboom et al., 2002; Hunter et al., 2004).

Neurological Inflammatory Diseases Following an Infection

Some neuropathies such as, e.g., acute disseminated encephalomyelitis usually follows a viral infection or viral vaccination (or, very rarely, bacterial vaccination), suggesting an immunologic cause to the disease. Acute inflammatory peripheral neuropathies that follow a viral vaccination or the Guillain-Barré syndrome are similar demyelinating disorders with the same presumed immunopathogenesis, but they affect only peripheral structures.

HTLV-associated myelopathy, a slowly progressive spinal cord disease associated with infection by the human T-cell lymphotrophic virus, is characterized by spastic weakness of both legs.

Central nervous system infections are extremely serious infections; meningitis affects the membranes surrounding the brain and spinal cord; encephalitis affects the brain itself. Viruses that infect the central nervous system (brain and spinal cord) include herpesviruses, arboviruses, coxsackieviruses, echoviruses, and enteroviruses. Some of these infections primarily affect the meninges (the tissues covering the brain) and result in meningitis; others primarily affect the brain and result in encephalitis; many affect both the meninges and brain and result in meningoencephalitis. Meningitis is far more common in children than is encephalitis. Viruses affect the central nervous system in two ways. They directly infect and destroy cells during the acute illness. After recovery from the infection, the body's immune response to the infection sometimes causes secondary damage to the cells around the nerves. This secondary damage (postinfectious encephalomyelitis) results in the child having symptoms several weeks after recovery from the acute illness.

Neurological Inflammatory Diseases Following Injuries

Injury to CNS induced by acute insults including trauma, hypoxia and ischemia can affect both grey and white matter. Injury to CNS involves neuro-inflammation. For example, leukocyte infiltration in the CNS after trauma or inflammation is triggered in part by up-regulation of the MCP-1 chemokine in astrocytes (Panenka et al., 2001).

Trauma is an injury or damage of the nerve. It may be spinal cord trauma, which is damage to the spinal cord that affects all nervous functions that are controlled at and below the level of the injury, including muscle control and sensation, or brain trauma, such as trauma caused by closed head injury.

Cerebral hypoxia is a lack of oxygen specifically to the cerebral hemispheres, and more typically the term is used to refer to a lack of oxygen to the entire brain. Depending on the severity of the hypoxia, symptoms may range from confusion to irreversible brain damage, coma and death.

Stroke is usually caused by reduced blood flow (ischemia) of the brain. It is also called cerebrovascular disease or accident. It is a group of brain disorders involving loss of brain functions that occurs when the blood supply to any part of the brain is interrupted. The brain requires about 20% of the circulation of blood in the body. The primary blood supply to the brain is through 2 arteries in the neck (the carotid arteries), which then branch off within the brain to multiple arteries that each supply a specific area of the brain. Even a brief interruption to the blood flow can cause decreases in brain function (neurological deficit). The symptoms vary with the area of the brain affected and commonly include such problems as changes in vision, speech changes, decreased movement or sensation in a part of the body, or changes in the level of consciousness. If the blood flow is decreased for longer than a few seconds, brain cells in the area are destroyed (infarcted) causing permanent damage to that area of the brain or even death. A stroke affects about 4 out of 1,000 people. It is the 3rd leading cause of death in most developed countries, including the U.S. The incidence of stroke rises dramatically with age, with the risk doubling with each decade after age 35. About 5% of people over age 65 have had at least one stroke. The disorder occurs in men more often than women. Causes of ischemic strokes are blood clots that form in the brain (thrombus) and blood clots or pieces of atherosclerotic plaque or other material that travel to the brain from another location (emboli). Bleeding (hemorrhage) within the brain may cause symptoms that mimic stroke. Strokes secondary to atherosclerosis (cerebral thrombosis) and strokes caused by embolism (moving blood clot) are the most common strokes.

Traumatic nerve injury may concern both the CNS or the PNS. Traumatic brain injury, also simply called head injury or closed head injury, refers to an injury where there is damage to the brain because of an external blow to the head. It mostly happens during car or bicycle accidents, but may also occur as the result of near drowning, heart attack, stroke and infections. This type of traumatic brain injury would usually result due to the lack of oxygen or blood supply to the brain, and therefore can be referred to as an "anoxic injury". Brain injury or closed head injury occurs when there is a blow to the head as in a motor vehicle accident or a fall. There may be a period of unconsciousness immediately following the trauma, which may last minutes, weeks or months. Primary brain damage occurs at the time of injury, mainly at the sites of impact, in particular when a skull fraction is present. Large contusions may be associated with an intracerebral haemorrhage, or accompanied by cortical lacerations. Diffuse axonal injuries occur as a result of shearing and tensile strains of neuronal processes produced by rotational movements of the brain within the skull. There may be small heamorrhagic lesions or diffuse damage to axons, which can only be detected microscopically. Secondary brain damage occurs as a result of complications developing after the moment of injury. They include intracranial hemorrhage, traumatic damage to extracerebral arteries, intracranial herniation, hypoxic brain damage or meningitis.

Spinal cord injuries account for the majority of hospital admissions for paraplegia and tetraplegia. Over 80% occur as a result of road accidents. Two main groups of injury are recognized clinically: open injuries and closed injuries. Open injuries cause direct trauma of the spinal cord and nerve roots. Perforating injuries can cause extensive disruption and hemorrhage. Closed injuries account for most spinal injuries and are usually associated with a fracture/dislocation of the spinal column, which is usually demonstrable radiologically. Damage to the cord depends on the extent of the bony injuries and can be considered in two main stages: primary damage, which are contusions, nerve fibre transections and hemorrhagic necrosis, and secondary damage, which are extradural heamatoma, infarction, infection and edema.

Peripheral Neuropathy

Peripheral Neuropathy is a syndrome of sensory loss, muscle weakness and atrophy, decreased deep tendon reflexes, and vasomotor symptoms, alone or in any combination. Peripheral Neuropathy is associated with axonal degeneration, a process also referred to as Wallerian degeneration. Neuro-inflammation plays a role in Wallerian degeneration (Stoll et al., 2002).

The disease may affect a single nerve (mononeuropathy), two or more nerves in separate areas (multiple mononeuropathy), or many nerves simultaneously (polyneuropathy). The axon may be primarily affected (e.g. in diabetes mellitus, Lyme disease, uremia or with toxic agents) or the myelin sheath or Schwann cell (e.g. in acute or chronic inflammatory polyneuropathy, leukodystrophies, or Guillain-Barré syndrome). Damage to small unmyelinated and myelinated fibers results primarily in loss of temperature and pain sensation; damage to large myelinated fibers results in motor or proprioceptive defects. Some neuropathies (e.g. due to lead toxicity, dapsone use, Lyme disease (caused by tick bite), porphyria, or Guillain-Barré syndrome) primarily affect motor fibers; others (e.g. due to dorsal root ganglionitis of cancer, leprosy, AIDS, diabetes mellitus, or chronic pyridoxine intoxication) primarily affect the dorsal root ganglia or sensory fibers, producing sensory symptoms. Occasionally, cranial nerves are also involved (e.g. in Guillain-Barré syndrome, Lyme disease, diabetes mellitus, and diphtheria). Identifying the modalities involved helps determine the cause.

Trauma is the most common cause of a localized injury to a single nerve. Violent muscular activity or forcible overextension of a joint may produce a focal neuropathy, as may repeated small traumas (e.g. tight gripping of small tools, excessive vibration from air hammers). Pressure or entrapment paralysis usually affects superficial nerves (ulnar, radial, peroneal) at bony prominences (e.g. during sound sleep or during anesthesia in thin or cachectic persons and often in alcoholics) or at narrow canals (e.g. in carpal tunnel syndrome). Pressure paralysis may also result from tumors, bony hyperostosis, casts, crutches, or prolonged cramped postures (e.g. in gardening). Hemorrhage into a nerve and exposure to cold or radiation may cause neuropathy. Mononeuropathy may result from direct tumor invasion.

Multiple mononeuropathy is usually secondary to collagen vascular disorders (e.g. polyarteritis nodosa, SLE, Sjögren's syndrome, RA), sarcoidosis, metabolic diseases (e.g. diabetes, amyloidosis), or infectious diseases (e.g. Lyme disease, HIV infection). Microorganisms may cause multiple mononeuropathy by direct invasion of the nerve (e.g. in leprosy).

Polyneuropathy due to acute febrile diseases may result from a toxin (e.g. in diphtheria) or an autoimmune reaction (e.g. in Guillain-Barré syndrome); the polyneuropathy that sometimes follows immunizations is probably also autoimmune.

Toxic agents generally cause polyneuropathy but sometimes mononeuropathy. They include emetine, hexobarbital, barbital, chlorobutanol, sulfonamides, phenyloin, nitrofurantoin, the vinca alkaloids, heavy metals, carbon monoxide, triorthocresyl phosphate, orthodinitrophenol, many solvents, other industrial poisons, and certain AIDS drugs (e.g. zalcitabine, didanosine).

Chemotherapy-induced neuropathy is a prominent and serious side effect of several commonly used chemotherapy medications, including the Vinca alkaloids (vinblastine, vincristine and vindesine), platinum-containing drugs (cisplatin) and Taxanes (paclitaxel). The induction of peripheral neuropathy is a common factor in limiting therapy with chemotherapeutic drugs.

Nutritional deficiencies and metabolic disorders may result in polyneuropathy. B vitamin deficiency is often the cause (e.g. in alcoholism, beriberi, pernicious anemia, isoniazid-induced pyridoxine deficiency, malabsorption syndromes, and hyperemesis gravidarum). Polyneuropathy also occurs in hypothyroidism, porphyria, sarcoidosis, amyloidosis, and uremia. Diabetes mellitus can cause sensorimotor distal polyneuropathy (most common), multiple mononeuropathy, and focal mononeuropathy (e.g. of the oculomotor or abducens cranial nerves).

Polyneuropathy due to metabolic disorders (e.g. diabetes mellitus) or renal failure develops slowly, often over months or years. It frequently begins with sensory abnormalities in the lower extremities that are often more severe distally than proximally. Peripheral tingling, numbness, burning pain, or deficiencies in joint proprioception and vibratory sensation are often prominent. Pain is often worse at night and may be aggravated by touching the affected area or by temperature changes. In severe cases, there are objective signs of sensory loss, typically with stocking-and-glove distribution. Achilles and other deep tendon reflexes are diminished or absent. Painless ulcers on the digits or Charcot's joints may develop when sensory loss is profound. Sensory or proprioceptive deficits may lead to gait abnormalities. Motor involvement results in distal muscle weakness and atrophy. The autonomic nervous system may be additionally or selectively involved, leading to nocturnal diarrhea, urinary and fecal incontinence, impotence, or postural hypotension. Vasomotor symptoms vary. The skin may be paler and drier than normal, sometimes with dusky discoloration; sweating may be excessive. Trophic changes (smooth and shiny skin, pitted or ridged nails, osteoporosis) are common in severe, prolonged cases.

Nutritional polyneuropathy is common among alcoholics and the malnourished. A primary axonopathy may lead to secondary demyelination and axonal destruction in the longest and largest nerves. Whether the cause is deficiency of thiamine or another vitamin (e.g. pyridoxine, pantothenic acid, folic acid) is unclear. Neuropathy due to pyridoxine deficiency usually occurs only in persons taking isoniazid for tuberculosis; infants who are deficient or dependent on pyridoxine may have convulsions. Wasting and symmetric weakness of the distal extremities is usually insidious but can progress rapidly, sometimes accompanied by sensory loss, paresthesias, and pain. Aching, cramping, coldness, burning, and numbness in the calves and feet may be worsened by touch. Multiple vitamins may be given when etiology is obscure, but they have no proven benefit.

Hereditary neuropathies are classified as sensorimotor neuropathies or sensory neuropathies. Charcot-Marie-Tooth disease is the most common hereditary sensorimotor neuropathy. Less common sensorimotor neuropathies begin at birth and result in greater disability. In sensory neuropathies, which are rare, loss of distal pain and temperature sensation is more prominent than loss of vibratory and position sense. The main problem is pedal mutilation due to pain insensitivity, with frequent infections and osteomyelitis. Hereditary neuropathies also include hypertrophic interstitial neuropathy and Dejerine-Sottas disease.

Malignancy may also cause polyneuropathy via monoclonal gammopathy (multiple myeloma, lymphoma), amyloid invasion, or nutritional deficiencies or as a paraneoplastic syndrome.

While of various etiologies, such as infectious pathogens or autoimmune attacks, neurological inflammatory diseases all cause loss of neurological function and may lead to paralysis and death. Although a few therapeutic agents reducing inflammatory attacks in some neurological inflammatory diseases are available, there is a need to develop novel therapies that could lead to recovery of neurological function.

2. STATs Signaling

The role of STATs signaling as modulator of pro- and anti-inflammatory response has been described in many biological systems (Pfitzner et al., 2004).

STAT2 activation can be mediated by interferon-β (INF-β). The STAT2 promoter has an interferon-stimulated response element (ISRE) (Yan et al., 1995). In human astrocytes, STAT2 activation decreases induction of the MCP-1 chemokine (Hua et al., 2002). Chemokines such as MCP-1 direct the recruitment of leukocytes to inflammatory sites and may also participate in the regulation of cytokine production by naive T helper cells. The beneficial effect of IFN-β via reduction of MCP-1 production in MS patients has been confirmed by ex vivo experiments (Comabella et al., 2002).

The physiological activities associated with MCP-1 have been extensively studied by means of transgenic animals and other animal models, which demonstrate that MCP-1 controls recruitment of monocytes and of other cell types (astrocytes, for example) in many infectious, inflammatory and autoimmune diseases, as well as the expression of cytokines related to T helper responses. MCP-1 was also shown to mediate parasitic infections caused by *Trichinella spiralis* (Conti and DiGioacchino, 2001). Therefore, in many pathological situations, MCP-1 is thought to enhance the inflammatory response by recruiting macrophages STAT2 activation, by leading to a decreased MCP-1 induction, is a promising way of treating disorders associated with neuro-inflammation.

3. The IL-18 Binding Protein (IL-18BP)

In 1989, an endotoxin-induced serum activity that induced interferon-γ (IFN-γ) obtained from mouse spleen cells was described (Nakamura et al., 1989). The factor responsible for this activity was named IFN-γ-inducing factor (IGIF) and later on interleukin-18 (IL-18). The human cDNA sequence for IL-18 was reported in 1996 (Ushio et al., 1996). Recombinant IL-18 induces IFN-γ more potently than does IL-12, apparently through a separate pathway (Micallef et al., 1996). IL-18 does not induce IFN-γ by itself, but functions primarily as a co-stimulant with mitogens or IL-2. IL-18 enhances T cell proliferation, apparently through an IL-2-dependent pathway, and enhances Th1 cytokine production in vitro and exhibits synergism when combined with IL-12 in terms of enhanced IFN-γ production (Maliszewski et al., 1990). IL-18 plays a potential role in immunoregulation or in inflammation by augmenting the functional activity of Fas ligand on Th1 cells (Conti et al., 1997). IL-18 is also expressed in the adrenal cortex and therefore might be a secreted neuro-immuno-modulator, playing an important role in orchestrating the immune system following a stressful experience (Chater, 1986). In addition, IL-18 expression is abnormally regulated in autoimmune NOD mice and closely associated with diabetes development (Rothe et al., 1997). In vivo, IL-18 is formed by cleavage of pro-IL-18, and its endogenous activity appears to account for IFN-γ production in P. acnes and LPS-mediated lethality. Mature IL-18 is produced from its precursor by the IL-1β converting enzyme (IL-1 beta-converting enzyme, ICE, caspase-1).

The IL-18 receptor consists of at least two components, co-operating in ligand binding. High- and low-affinity binding sites for IL-18 were found in murine IL-12 stimulated T cells suggesting a multiple chain receptor complex (Yoshimoto et al., 1998). Two receptor subunits have been identified so far, both belonging to the IL-1 receptor family (Parnet et al., 1996). The signal transduction of IL-18 involves activation of NF-κB (DiDonato et al., 1997).

Recently, a soluble protein having a high affinity for IL-18 has been isolated from human urine, and the human and mouse cDNAs were described (Novick et al., 1999c) (WO 99/09063). The protein has been designated IL-18 binding protein (IL-18BP).

IL-18BP is not the extracellular domain of one of the known IL-18 receptors, but a secreted, naturally circulating protein. It belongs to a novel family of secreted proteins. The family further includes several Poxvirus-encoded proteins which have a high homology to IL-18BP (Novick et al., 1999b). IL-18BP is constitutively expressed in the spleen, belongs to the immunoglobulin superfamily, and has limited homology to the IL-1 type II receptor. Its gene was localized on human chromosome 11q13, and no exon coding for a transmembrane domain was found in an 8.3 kb genomic sequence (Novick et al., 1999a).

Four human and two mouse isoforms of IL-18BP, resulting from mRNA splicing and found in various cDNA libraries and have been expressed, purified, and assessed for binding and neutralization of IL-18 biological activities (Kim et al., 2000b). Human IL-18BP isoform a (IL-18BPa) exhibited the greatest affinity for IL-18 with a rapid on-rate, a slow off-rate, and a dissociation constant (K(d)) of 399 pM. IL-18BPc shares the Ig domain of IL-18BPa except for the 29 C-terminal amino acids; the K(d) of IL-18BPc is 10-fold less (2.94 nM). Nevertheless, IL-18BPa and IL-18BPc neutralize IL-18 >95% at a molar excess of two. Human IL-18BPb and IL-18BPd isoforms lack a complete Ig domain and lack the ability to bind or neutralize IL-18. Molecular modeling identified a large mixed electrostatic and hydrophobic binding site in the Ig domain of IL-18BP, which could account for its high affinity binding to the ligand (Kim et al., 2000a).

IL-18BPa and IL-18BPc acting as IL-18 inhibitors, these isoforms have been proposed as potential therapeutics for treating diseases associated with an immune response linked with IL-18 activity. However, the beneficial effect of IL-18BP isoforms in non-IL-18-associated diseases has not yet been suggested. In addition, the biological significance of the IL-18BPb and IL-18BPd isoforms is poorly understood in the prior art.

SUMMARY OF THE INVENTION

It is the object of the present invention to provide novel means for the treatment and/or prevention of a neurological and/or inflammatory disease.

The present invention is based on the finding that IL-18BPb and IL-18BPd diminished the secretion both of the IL-6 pro-inflammatory cytokine and of the MCP-1 chemokine in astroglial cells co-stimulated by IL-1β and IFN-γ. Experiments showed that unlike IL-18BPa and IL-18BPc, IL-18BPb and IL-18BPd induced STAT2 nuclear translocation in glioblastoma cells, STAT2 being a factor that acts as a modulator of the inflammatory response. It was further shown in the frame of the present invention that IL-18BPb and IL-18BPd significantly protect fibroblast cells from Trail-induced apoptosis.

Therefore, a first aspect of the invention relates to the use of an IL-18BP isoform that does not bind to IL-18, or of an agonist of said IL-18BP isoform, for the manufacture of a medicament for the treatment and/or the prevention of a neurological and/or inflammatory disease.

A second aspect relates to the use of a nucleic acid molecule for manufacture of a medicament for the treatment and/or prevention of a neurological and/or inflammatory disease, wherein the nucleic acid molecule comprises a nucleic acid sequence encoding an IL-18BP isoform that does not bind to IL-18.

A third aspect relates to the use of a vector for inducing and/or enhancing the endogenous production of an IL-18BP isoform that does not bind to IL-18, or of an agonist of said IL-18BP isoform, in a cell in the manufacture of a medicament for the treatment and/or prevention of a neurological and/or inflammatory disease.

A fourth aspect relates to the use of a cell that has been genetically modified to produce an IL-18BP isoform that does not bind to IL-18, or of an agonist of said IL-18BP isoform, in the manufacture of a medicament for the treatment and/or prevention of a neurological and/or inflammatory disease.

A fifth aspect relates to a method for treating a neurological and/or inflammatory disease comprising administering to a patient in need thereof an effective amount of an IL-18BP isoform that does not bind to IL-18, or of an agonist of said IL-18BP isoform, optionally together with a pharmaceutically acceptable carrier.

BRIEF DESCRIPTION OF THE DRAWINGS

FIG. 2 shows the amino acid sequence of the human IL-18BPa, IL-18BPb, IL-18BPc and IL-18BPd isoforms.

FIG. 3A shows the effect of IL-18BPb and IL-18BPd on STAT2 nuclear translocation in human U373 astroglioma cells.

FIG. 5A shows the effect of IL-18BPb on MCP-1 secretion by U373 cells stimulated by IL-1β and IFNγ, 48 hrs after stimulation. Significance was calculated versus stimulated cells not treated with IL-18BPb, *p<0.05, p<0.005, *p<0.001.

BRIEF DESCRIPTION OF THE SEQUENCES

Figure 1:
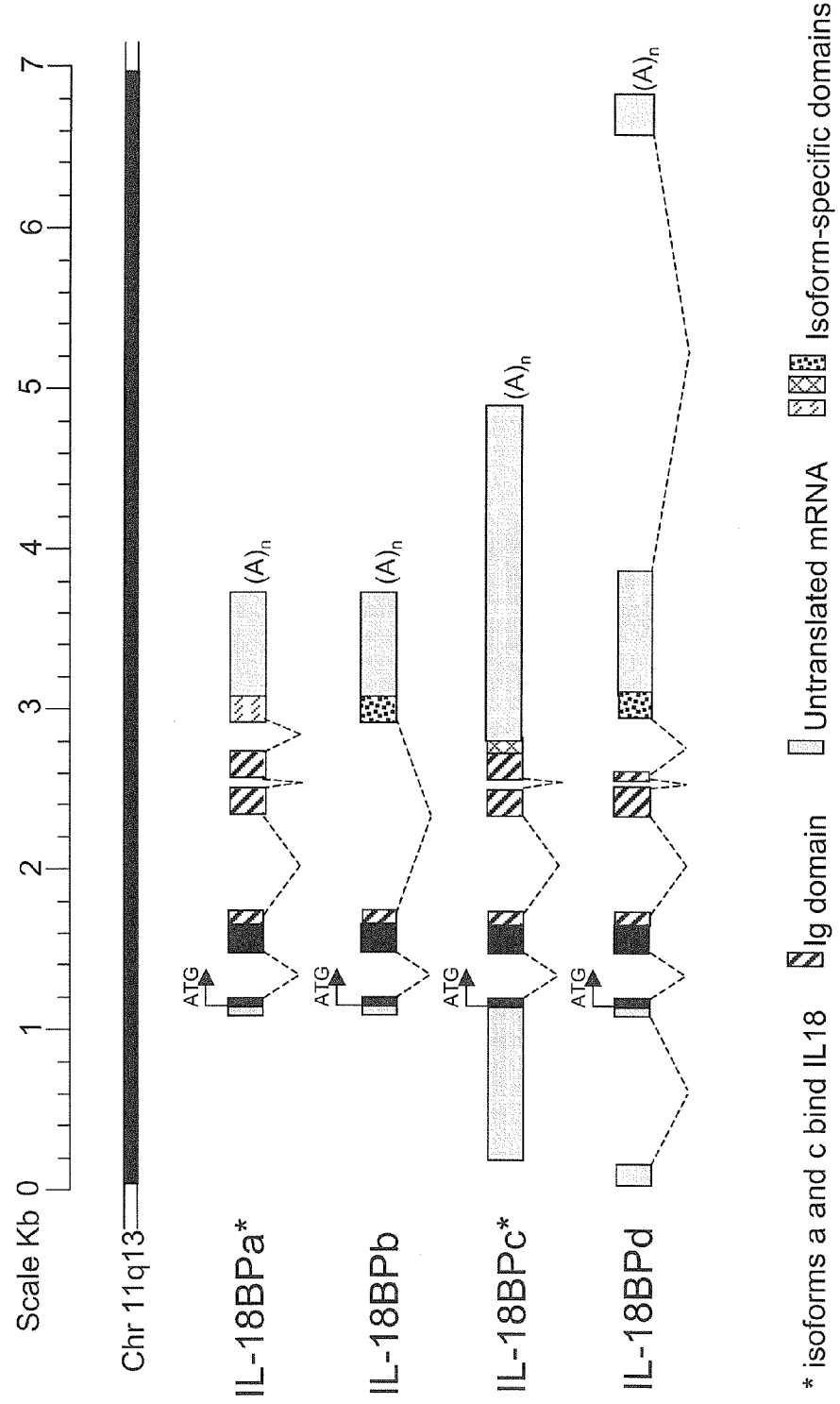
FIG. 1 schematically depicts the structure of the human IL-18BP gene, and of the human IL-18BPa, IL-18BPb, IL-18BPc and IL-18BPd splice isoforms.

SEQ ID NO: 1 corresponds to the amino acid sequence of the IL-18BPb isoform.
SEQ ID NO: 2 corresponds to the amino acid sequence of the IL-18BPd isoform.
SEQ ID NO: 3 corresponds to the amino acid sequence of the IL-18BPa isoform.
SEQ ID NO: 4 corresponds to the amino acid sequence of the IL-18BPc isoform.
SEQ ID NO: 5-12 correspond to the nucleotide sequence of the primers used in Example 5.

DETAILED DESCRIPTION OF THE INVENTION

In the frame of the present invention, it has been found that that IL-18BPb and IL-18BPd diminished the secretion both of the IL-6 pro-inflammatory cytokine and of the MCP-1 chemokine in astroglial cells co-stimulated by IL-1β and IFN-γ.

In addition to this, it has been shown that unlike IL-18α and IL-18c, IL-18BPb and IL-18BPd induce STAT2 nuclear translocation in glioblastoma cells, STAT2 being a factor that acts as a modulator of the inflammatory response.

The invention is also based on the finding that IL-18BPb and IL-18BPd significantly protect fibroblast cells from Trail-induced apoptosis.

The experimental evidence presented herein therefore provides for a new possibility of treating neurological and/or inflammatory diseases.

The invention therefore relates to the use of an IL-18BP isoform that does not bind to IL-18, or of an agonist of said IL-18BP isoform, for the manufacture of a medicament for treatment and/or prevention of neurological and/or inflammatory diseases.

The term "IL-18BP", as used herein, relates to IL-18 binding proteins as defined in WO 99/09063 or in Novick et al. (1999) including splice variants and/or isoforms of IL-18 binding proteins. The term "IL-18BP", as used herein, further encompasses muteins, fused proteins, functional derivatives, active fractions or fragments, or circularly permutated derivatives, or salts thereof. Four different human isoforms are currently known: IL-18BPa, IL-18BPb, IL-18BPc and IL-18BPd. These isoforms are defined in Kim et al. (2000). IL-18BPb corresponds to SEQ ID NO: 1, IL-18BPd corresponds to SEQ ID NO: 2, IL-18BPa corresponds to SEQ ID NO: 3 and IL-18BPc corresponds to SEQ ID NO: 4.

As used herein, the term "IL-18BP isoform that does not bind to IL-18" refers to an isoform of IL-18BP that lacks the ability to bind and/or neutralize IL-18 as defined in Kim et al. (2000). The term "IL-18BP isoform that does not bind to IL-18" refers to naturally occurring polypeptides as well as to muteins, salts, fused proteins functional derivatives active fractions or circularly permutated derivatives thereof. Naturally occurring IL-18BP isoforms that do not bind to IL-18 include human IL-18BPb and human IL-18BPd. An "IL-18BP isoform that does not bind to IL-18" may also be referred to as an "IL-18BP isoform in accordance with the invention".

The ability of an IL-18BP isoform to bind IL-18 can for example be measured using a BIAcore sensor chip with immobilized mature IL-18 as disclosed, as described in of Kim et al. (2000). Such a method allows calculation of the mean dissociation constant, of the association rate and of the dissociation rate. The ability of an IL-18BP isoform to neutralize IL-18 can for example be measured by measuring the effect of the IL-18BP isoform on IL-18 biological activity in an assay such as, e.g., those listed in the paragraph entitled "Human and Mouse IL-18 assays" at pages 1190-1191 of Kim et al. (2000). Alternatively, the ability of an IL-18BP isoform to neutralize IL-18 can be measured as taught in the paragraph entitled "Titration of IL-18BP Activity" at page 1192 of Kim et al. (2000).

The term "agonist of an IL-18BP isoform that does not bind to IL-18" as used herein, relates to a molecule stimulating or imitating activity of an IL-18BP isoform that does not bind to IL-18. Such agonists encompass agents enhancing activities mediated by IL-18BP isoforms that do not bind to IL-18, such as promotion of STAT2 nuclear translocation, inhibition of secretion of IL-6 and of MCP-1, and/or protection from Trail-induced apoptosis. All methods and uses disclosed herein may be carried either with an IL-18BP isoform that does not bind to IL-18, or with an agonist thereof.

The terms "treating" and "preventing", as used herein, should be understood as preventing, inhibiting, attenuating, ameliorating or reversing one or more symptoms or cause(s) of neurological and/or inflammatory disease, as well as symptoms, diseases or complications accompanying neurological and/or inflammatory disease. When "treating" neurological and/or inflammatory disease, the substances according to the invention are given after onset of the disease, "prevention" relates to administration of the substances before signs of disease can be noted in the patient.

The term "neurological and/or inflammatory diseases", as used herein encompasses all known neurological and/or inflammatory diseases or disorders, or injuries of the CNS or PNS. Preferably, said neurological and/or inflammatory disease is a neurological disease associated with neuro-inflammation, referred to as a "neurological inflammatory disease". These diseases include those described in detail in the "Background of the invention".

Neurological and/or inflammatory diseases comprise disorders linked to dysfunction of the CNS or PNS, such as diseases related to neurotransmission, headache, trauma of the head, CNS infections, neuro-opthalmologic and cranial nerve disorders, function and dysfunction of the cerebral lobes disorders of movement, stupor and coma, demyelinating diseases, delirium and dementia, craniocervical junction abnormalities, seizure disorders, spinal cord disorders, sleep disorders, disorders of the peripheral nervous system, cerebrovascular disease, or muscular disorders. For definitions of these disorders, see e.g. The Merck Manual for Diagnosis and Therapy, Seventeenth Edition, published by Merck Research Laboratories, 1999.

Preferably, the neurological and/or inflammatory diseases of the invention are selected from the group consisting of traumatic nerve injury, stroke, demyelinating diseases of the CNS or PNS, neuropathies and chronic neurodegenerative diseases.

Traumatic nerve injury may concern the PNS or the CNS, it may be brain or spinal cord trauma, including paraplegia, as described in the "background of the invention" above.

Stroke may be caused by hypoxia or by ischemia of the brain. It is also called cerebrovascular disease or accident. Stroke may involve loss of brain functions (neurological deficits) caused by a loss of blood circulation to areas of the brain. Loss of blood circulation may be due to blood clots that form in the brain (thrombus), or pieces of atherosclerotic plaque or other material that travel to the brain from another location (emboli). Bleeding (hemorrhage) within the brain may cause symptoms that mimic stroke. The most common cause of a stroke is stroke secondary to atherosclerosis (cerebral thrombosis), and therefore the invention also relates to the treatment of atherosclerosis.

Peripheral Neuropathy may be related to a syndrome of sensory loss, muscle weakness and atrophy, decreased deep tendon reflexes, and vasomotor symptoms, alone or in any combination. Neuropathy may affect a single nerve (mononeuropathy), two or more nerves in separate areas (multiple mononeuropathy), or many nerves simultaneously (polyneuropathy). The axon may be primarily affected (e.g. in diabetes mellitus, Lyme disease, or uremia or with toxic agents), or the myelin sheath or Schwann cell (e.g. in acute or chronic inflammatory polyneuropathy, leukodystrophies, or Guillain-Barré syndrome). Further neuropathies, which may be treated in accordance with the present invention, may e.g. be due to lead toxicity, dapsone use, tick bite, porphyria, or Guillain-Barré syndrome, and they may primarily affect motor fibers. Others, such as those due to dorsal root ganglionitis of cancer, leprosy, AIDS, diabetes mellitus, or chronic pyridoxine intoxication, may primarily affect the dorsal root ganglia or sensory fibers, producing sensory symptoms. Cranial nerves may also be involved, such as e.g. in Guillain-Barré syndrome, Lyme disease, diabetes mellitus, and diphtheria.

Alzheimer's disease is a disorder involving deterioration in mental functions resulting from changes in brain tissue. This may include shrinking of brain tissues, primary degenerative dementia and diffuse brain atrophy. Alzheimer's disease is also called senile dementia/Alzheimer's type (SDAT).

Parkinsons's disease is a disorder of the brain including shaking and difficulty with walking, movement, and coordination. The disease is associated with damage to a part of the brain that controls muscle movement, and it is also called paralysis agitans or shaking palsy.

Huntington's Disease is an inherited, autosomal dominant neurological inflammatory disease. The genetic abnormality consists in an excess number of tandemly repeated CAG nucleotide sequences. Other diseases with CAG repeats include, for example, spinal muscular atrophies (SMA), such as Kennedy's disease, and most of the autosomal dominant cerebellar ataxias (ADCAs) that are known as spinocerebellar ataxias (SCAs) in genetic nomenclature.

Amyotrophic Lateral Sclerosis, ALS, is a disorder causing progressive loss of nervous control of voluntary muscles, including of destruction of nerve cells in the brain and spinal cord. Amyotrophic Lateral Sclerosis, also called Lou Gehrig's disease, is a disorder involving loss of the use and control of muscles.

Multiple Sclerosis (MS) is an inflammatory disease of the central nervous system (CNS) that takes a relapsing-remitting or a progressive course. MS is not the only demyelinating disease. Its counterpart in the peripheral nervous system (PNS) is chronic inflammatory demyelinating polyradiculoneuropathy (CIDP). In addition, there are acute, monophasic disorders, such as the inflammatory demyelinating polyradiculoneuropathy termed Guillain-Barré syndrome (GBS) in the PNS, and acute disseminated encephalomyelitis (ADEM) in the CNS.

Neurological and/or inflammatory diseases may further be due to congenital metabolic disorders. In a preferred embodiment of the invention, the neurological and/or inflammatory disease is therefore due to a congenital metabolic deficit. The congenital metabolic disorders encompassed by the present invention may be e.g. diabetes, phenylketonuria and other aminoacidurias, Tay-Sachs, Niemann-Pick, and Gaucher's diseases, Hurler's syndrome; Krabbe's disease and other leukodystrophies. They may affect the developing myelin sheath, mainly in the CNS.

Less well-known neurological inflammatory diseases are also within the scope of the present invention, such as neurofibromatosis, or Multiple System Atrophy (MSA). Further disorders that may be treated in accordance with the present invention, have been described in detail in the "Background of the invention" above.

In a further preferred embodiment, the neurological and/or inflammatory disease is a peripheral neuropathy, most preferably diabetic neuropathy. Chemotherapy associated/induced neuropathies are also preferred in accordance with the present invention. The term "diabetic neuropathy" relates to any form of diabetic neuropathy, or to one or more symptom(s) or disorder(s) accompanying or caused by diabetic neuropathy, or complications of diabetes affecting nerves as described in detail in the "Background of the invention" above. Diabetic neuropathy may be a polyneuropathy. In diabetic polyneuropathy, many nerves are simultaneously affected. The diabetic neuropathy may also be a mononeuropathy. In focal mononeuropathy, for instance, the disease affects a single nerve, such as the oculomotor or abducens cranial nerve. It may also be multiple mononeuropathy when two or more nerves are affected in separate areas.

In yet a further preferred embodiment, the neurological and/or inflammatory disease is a demyelinating disease. Demyelinating diseases preferably comprise demyelinating conditions of the CNS, like acute disseminated encephalomyelitis (ADEM) and multiple sclerosis (MS), as well as demyelinating diseases of the peripheral nervous system (PNS). The latter comprise diseases such as chronic inflammatory demyelinating polyradiculoneuropathy (CIDP and acute, monophasic disorders, such as the inflammatory demyelinating polyradiculoneuropathy termed Guillain-Barré syndrome (GBS).

A further preferred embodiment of the invention relates to the treatment and/or prevention of a neurodegenerative disease. The neurodegenerative disease is selected from the group consisting of Alzheimer's disease, Parkinson's disease, Huntington's disease and ALS.

Preferably, the IL-18BP isoform that does not bind to IL-18 is selected from the group consisting of:
  a) A polypeptide comprising SEQ ID NO: 1;
  b) A polypeptide comprising amino acids 29 to 113 of SEQ ID NO: 1;
  c) A polypeptide comprising amino acids 78 to 113 of SEQ ID NO: 1;

d) A polypeptide comprising SEQ ID NO: 2;

e) A polypeptide comprising amino acids 29 to 161 of SEQ ID NO: 2;

f) A mutein of any of (a) to (e), wherein the amino acid sequence has at least 75%, 80%, 85%, 90%, 95%, 96%, 97%, 98% or 99% identity to at least one of the sequences in (a) to (e);

g) A mutein of any of (a) to (e) which is encoded by a DNA sequence which hybridizes to the complement of the native DNA sequence encoding any of (a) to (e) under moderately stringent conditions or under highly stringent conditions;
h) A mutein of any of (a) to (e) wherein any changes in the amino acid sequence are conservative amino acid substitutions to the amino acid sequences in (a) to (e);
i) a salt or a fused protein, functional derivative, active fraction or circularly permutated derivative of any of (a) to (h).

The person skilled in the art will further appreciate that muteins, allelic variants salts, fused proteins, functional derivatives of an IL-18BP isoform in accordance with the present invention, active fractions or circularly permutated derivatives of a naturally occurring IL-18BP isoform in accordance with the present invention, will retain a similar, or even better, biological activity than said naturally occurring isoform.

Preferred active fractions have an activity which is equal or better than the activity of IL-18BPb or IL-18BPd, or which have further advantages, such as a better stability or a lower toxicity or immunogenicity, or they are easier to produce in large quantities, or easier to purify. The person skilled in the art will appreciate that muteins, active fragments and functional derivatives can be generated by cloning the corresponding cDNA in appropriate plasmids and testing them in the co-culturing assay, as mentioned above.

The proteins according to the present invention may be glycosylated or non-glycosylated, they may be derived from natural sources, such as body fluids, or they may preferably be produced recombinantly. Recombinant expression may be carried out in prokaryotic expression systems such as *E. coli*, or in eukaryotic, such as insect cells, and preferably in mammalian expression systems, such as CHO-cells or HEK-cells.

As used herein the term "muteins" refers to analogs of IL-18BPb or IL-18BPd, in which one or more of the amino acid residues of the natural IL-18-BP isoform are replaced by different amino acid residues, or are deleted, or one or more amino acid residues are added to the natural sequence of the IL-18-BP isoform, without changing considerably the activity of the resulting products as compared with the wild-type IL-18BP isoform. These muteins are prepared by known synthesis and/or by site-directed mutagenesis techniques, or any other known technique suitable therefore. The term "muteins" encompasses naturally-occurring allelic variants of an IL-18BPb polypeptide of SEQ ID NO: 1 and/or naturally-occurring allelic variants of an IL-18BPd polypeptide of SEQ ID NO: 2.

Muteins of an IL-18BP isoform in accordance with the present invention, which can be used in accordance with the present invention, or nucleic acid coding thereof, include a finite set of substantially corresponding sequences as substitution peptides or polynucleotides which can be routinely obtained by one of ordinary skill in the art, without undue experimentation, based on the teachings and guidance presented herein.

Muteins in accordance with the present invention include proteins encoded by a nucleic acid, such as DNA or RNA, which hybridizes to DNA or RNA, which encodes an IL-18BP isoform in accordance with the present invention, under moderately or highly stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

In a preferred embodiment, any such mutein has at least 40% identity with the sequence of SEQ ID NO: 1 or with the sequence of SEQ ID NO: 2 of the annexed sequence listing. More preferably, it has at least 50%, 55%, 60%, 65%, 70%, 75%, 80%, 85% or, most preferably, at least 90%, 95%, 96%, 97%, 98% or 99% identity thereto.

In another preferred embodiment, such mutein has at least 40% identity with the sequence of a naturally occurring IL-18BP isoform that does not bind to IL-18BP. More preferably, it has at least 50%, 55%, 60%, 65%, 70%, 75%, 80%, 85% or, most preferably, at least 90%, 95%, 96%, 97%, 98% or 99% identity thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called "global alignment"), that is particularly suitable for sequences of the same or very similar length, or over shorter, defined lengths (so-called "local alignment"), that is more suitable for sequences of unequal length. In the frame of the present invention, the "% of identity" refers to the global percent of identity that has been determined over the whole length of each of the sequences being compared.

Known computer programs may be used to determine whether any particular polypeptide is a percentage identical to a sequence of the present invention. Such algorithms and programs include, e.g. TBLASTN, BLASTP, FASTA, TFASTA, and CLUSTALW (Altschul et al., 1990a; Altschul et al., 1997a; Higgins et al., 1996; Pearson and Lipman, 1988; Thompson et al., 1994). Protein and nucleic acid sequence homologies are preferably evaluated using the Basic Local Alignment Search Tool ("BLAST"), which is well known in the art (Altschul et al., 1990b; Altschul et al., 1997b; Karlin and Altschul, 1990b)).

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. The scoring matrix used may be the BLO- SUM62 matrix (Gonnet et al., 1992; Henikoff and Henikoff, 1993). The PAM or PAM250 matrices may also be used (See, e.g., Schwartz and Dayhoff, eds, (1978) Matrices for Detecting Distance Relationships Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (Karlin and Altschul, 1990a). The BLAST programs may be used with the default parameters or with modified parameters provided by the user.

A preferred method for determining the best overall match between a query sequence (a sequence of the present invention) and a subject sequence, also referred to as a global sequence alignment, can be determined using the FASTDB computer program based on the algorithm of Brutlag (Brutlag et al., 1990). In a sequence alignment the query and subject sequences are both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group=25 Length=0, Cutoff Score=1, Window Size=sequence length, Gap Penalty=5, Gap Size Penalty=0.05, Window Size=247 or the length of the subject amino acid sequence, whichever is shorter.

If the subject sequence is shorter than the query sequence due to N- or C-terminal deletions, not because of internal deletions, the results, in percent identity, must be manually corrected because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, that are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100-residue query sequence to determine percent identity. The deletion occurs at the N-terminus of the subject sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%.

Preferred changes for muteins in accordance with the present invention are what are known as "conservative" substitutions. Conservative amino acid substitutions of IL-18BP isoforms in accordance with the present invention, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g. under thirty, and preferably under ten, and do not remove or displace amino acids which are critical to a functional conformation, e.g. cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of a naturally occurring IL-18BP isoform in accordance with the present invention, for use in the present invention include any known method steps, such as presented in U.S. Pat. Nos. 4,959,314, 4,588,585 and 4,737,462, to Mark et al; 5,116,943 to Koths et al., 4,965,195 to Namen et al; 4,879,111 to Chong et al; and 5,017,691 to Lee et al; and lysine substituted proteins presented in U.S. Pat. No. 4,904,584 (Shaw et al).

The term "fused protein" refers to a polypeptide comprising a naturally occurring IL-18BP isoform in accordance with the present invention, or a mutein or fragment thereof, fused with another protein, which e.g. has an extended residence time in body fluids. The IL-18BP isoform in accordance with the present invention may thus be fused to another protein, polypeptide or the like, e.g. an immunoglobulin or a fragment thereof. Immunoglobulin Fc portions are particularly suitable for production of di- or mulitmeric Ig fusion proteins. The IL-18BP isoform in accordance with the present invention may e.g. be linked to portions of an immunoglobulin in such a way as to produce a IL-18BP isoform in accordance with the present invention dimerized by the Ig Fc portion. In another embodiment, the sequence of the IL-18BP isoform in accordance with the present invention is fused to a signal peptide and/or to a leader sequence allowing enhanced secretion. The leader sequence may for example corresponds to the IgSP-tPA pre-propeptide disclosed in PCT application PCT/EP2004/052302.

"Functional derivatives" as used herein, cover derivatives of naturally occurring IL-18BP isoform in accordance with the present invention, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-18BPb and/or IL-18BPd, and do not confer toxic properties on compositions containing it.

These derivatives may, for example, include polyethylene glycol side-chains, which may mask antigenic sites and extend the residence of IL-18BP isoforms in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of naturally occurring IL-18BP isoforms in accordance with the present invention, muteins and fused proteins, the present invention covers any fragment or precursors of the polypeptide chain of the protein molecule alone or together with associated molecules or residues linked thereto, e.g. sugar or phosphate residues, or aggregates of the protein molecule or the sugar residues by themselves, provided said fraction has substantially similar activity to IL-18BPb and/or IL-18BPd.

The term "salts" herein refers to both salts of carboxyl groups and to acid addition salts of amino groups of an IL-18BP isoform in accordance with the present invention or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the IL-18BP isoform relevant to the present invention.

Functional derivatives of IL-18BP isoforms in accordance with the present invention IL-18BP isoforms in accordance with the present invention may be conjugated to polymers in order to improve the properties of the protein, such as the stability, half-life, bioavailability, tolerance by the human body, or immunogenicity. To achieve this goal, an IL-18BP isoform in accordance with the present invention may be linked e.g. to Polyethlyenglycol (PEG). PEGylation may be carried out by known methods, described in WO 92/13095, for example.

Therefore, in a preferred embodiment of the present invention, the IL-18BP isoform in accordance with the present invention is PEGylated.

In a further preferred embodiment of the invention, the fused protein comprises an immunoglobulin (Ig) fusion. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO: 13) introduced between the IL-18BP isoform sequence and the immunoglobulin sequence, for instance. The resulting fusion protein has improved properties, such as an extended residence time in body fluids (half-life), or an increased specific activity, increased expression level. The Ig fusion may also facilitate purification of the fused protein.

In a yet another preferred embodiment, an IL-18BP isoform in accordance with the present invention is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms $IgG_2$ or $IgG_4$, or other Ig classes, like IgM, for example. Fusion proteins may be monomeric or multimeric, hetero- or homomultimeric. The immunoglobulin portion of the fused protein may be further modified in a way as to not activate complement binding or the complement cascade or bind to Fc-receptors.

The invention further relates to the use of a combination of an IL-18BP isoform in accordance with the present invention and an immunosuppressive agent for the manufacture of a medicament for treatment and/or prevention of a neurological and/or inflammatory disease, for simultaneous, sequential or separate use. Immunosuppressive agents may be steroids, methotrexate, cyclophosphamide, anti-leukocyte antibodies (such as CAMPATH-1), and the like.

The invention further relates to the simultaneous, sequential, or separate use of:
- (i) an IL-18BP isoform that does not bind to IL-18, or of an agonist of said IL-18BP isoform; and
- (ii) a polypeptide selected from the group consisting of an interferon, osteopontin and clusterin for the manufacture of a medicament for the treatment and/or the prevention of a neurological and/or inflammatory disease.

The term "interferon", as used in the present patent application, is intended to include any molecule defined as such in the literature, comprising for example any kinds of IFNs mentioned in the above section "Background of the Invention". The interferon may preferably be human, but also derived from other species, as long as the biological activity is similar to human interferons, and the molecule is not immunogenic in man. In particular, any kinds of IFN-α, IFN-β and IFN-γ are included in the above definition. IFN-β, and more specifically IFN-β1a, is the preferred IFN according to the present invention. The term "interferon-beta (IFN-β)", as used in the present invention, is intended to include human fibroblast interferon, as obtained by isolation from biological fluids or as obtained by DNA recombinant techniques from prokaryotic or eukaryotic host cells as well as its salts, functional derivatives, variants, analogs and fragments. Interferons may also be conjugated to polymers in order to improve the stability of the proteins. A conjugate between Interferon β and the polyol polyethlyenglycol (PEG) has been described in WO99/55377, for instance.

"Osteopontin", as used herein, encompasses also muteins, fragments, active fractions and functional derivatives of osteopontin. These proteins are described e.g. in WO 02/092122.

"Clusterin", as used herein, encompasses also muteins, fragments, active fractions and functional derivatives of clusterin. These proteins are described e.g. in WO 04/084932.

In a preferred embodiment of the present invention, the IL-18BP isoform in accordance with the present invention is used in an amount of:
- a) about 0.001 to 100 mg/kg of body weight; or
- b) about 0.01 to 10 mg/kg of body weight; or
- c) about 0.1 to 1 mg/kg of body weight; or
- d) about 9, 8, 7, 6, 5, 4, 3, 2 or 1 mg/kg of body weight.

The invention further relates to the use of a nucleic acid molecule for manufacture of a medicament for the treatment and/or prevention of a peripheral neurologically disease, wherein the nucleic acid molecule comprises a nucleic acid sequence encoding a polypeptide comprising an amino acid sequence selected from the group consisting of:
- a) A polypeptide comprising SEQ ID NO: 1;
- b) A polypeptide comprising amino acids 29 to 113 of SEQ ID NO: 1;
- c) A polypeptide comprising amino acids 78 to 113 of SEQ ID NO: 1;
- d) A polypeptide comprising SEQ ID NO: 2;
- e) A polypeptide comprising amino acids 29 to 161 of SEQ ID NO: 2;
- f) A mutein of any of (a) to (e), wherein the amino acid sequence has at least 75%, 80%, 85%, 90%, 95%, 96%, 97%, 98% or 99% identity to at least one of the sequences in (a) to (e);
- g) A mutein of any of (a) to (e) which is encoded by a DNA sequence which hybridizes to the complement of the native DNA sequence encoding any of (a) to (e) under moderately stringent conditions or under highly stringent conditions;
- h) A mutein of any of (a) to (e) wherein any changes in the amino acid sequence are conservative amino acid substitutions to the amino acid sequences in (a) to (e);
- i) a salt or a fused protein, functional derivative, active fraction or circularly permutated derivative of any of (a) to (h).

The nucleic acid may e.g. be administered as a naked nucleic acid molecule, e.g. by intramuscular injection.

It may further comprise vector sequences, such as viral sequence, useful for expression of the gene encoded by the nucleic acid molecule in the human body, preferably in the appropriate cells or tissues.

Therefore, in a preferred embodiment, the nucleic acid molecule further comprises an expression vector sequence. Expression vector sequences are well known in the art, they comprise further elements serving for expression of the gene of interest. They may comprise regulatory sequence, such as promoter and enhancer sequences, selection marker sequences, origins of multiplication, and the like. A gene therapeutic approach is thus used for treating and/or preventing the disease. Advantageously, the expression of the IL-18BP isoform in accordance with the present invention will then be in situ.

In a preferred embodiment of the invention, the expression vector may be administered by intramuscular injection.

The use of a vector for inducing and/or enhancing the endogenous production of an IL-18BP isoform in accordance with the invention in a cell normally silent for expression of said IL-18BP isoform, or which expresses amounts of said IL-18BP isoform which are not sufficient, are also contemplated according to the invention. The vector may comprise regulatory sequences functional in the cells desired to express the IL-18BP isoform in accordance with the present invention. Such regulatory sequences may be promoters or enhancers, for example. The regulatory sequence may then be introduced into the appropriate locus of the genome by homologous recombination, thus operably linking the regulatory sequence with the gene, the expression of which is required to be induced or enhanced. The technology is usually referred to as "endogenous gene activation" (EGA), and it is described e.g. in WO 91/09955.

The invention further relates to the use of a cell that has been genetically modified to produce an IL-18BP isoform in accordance with the invention in the manufacture of a medicament for the treatment and/or prevention of peripheral neurologically diseases.

The invention further relates to a cell that has been genetically modified to produce an IL-18BP isoform in accordance with the invention for manufacture of a medicament for the treatment and/or prevention of neurologically diseases. Thus, a cell therapeutic approach may be used in order to deliver the drug to the appropriate parts of the human body.

The invention further relates to pharmaceutical compositions, particularly useful for prevention and/or treatment of neurological and/or inflammatory diseases, which comprise:
- a) a therapeutically effective amount of an IL-18BP isoform in accordance with the invention, or of an agonist thereof;

b) a pharmaceutically acceptable carrier; and optionally
c) a therapeutically effective amount of an immuno-suppressant.

The immunosuppressant may for example be a polypeptide selected from the group consisting of an interferon, osteopontin and clusterin.

The definition of "pharmaceutically acceptable carrier" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, epidural, topical, intrathecal, rectal, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilised powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The therapeutically effective amounts of the active protein(s) will be a function of many variables, including the type of protein, the affinity of the protein, any residual cytotoxic activity exhibited by the antagonists, the route of administration, the clinical condition of the patient (including the desirability of maintaining a non-toxic level of endogenous IL-18BP activity).

A "therapeutically effective amount" is such that when administered, the IL-18BP isoform in accordance with the present invention exerts a beneficial effect on the neurological and/or inflammatory disease. The dosage administered, as single or multiple doses, to an individual will vary depending upon a variety of factors, including IL-18BP pharmacokinetic properties, the route of administration, patient conditions and characteristics (sex, age, body weight, health, size), extent of symptoms, concurrent treatments, frequency of treatment and the effect desired.

The IL-18BP isoform in accordance with the invention can preferably be used in an amount of about 0.001 to 10 mg/kg or about 0.01 to 5 mg/kg or body weight or about 0.1 to 3 mg/kg of body weight or about 1 to 2 mg/kg of body weight. Further preferred amounts of IL-18BP are amounts of about 0.1 to 1000 µg/kg of body weight or about 1 to 100 µg/kg of body weight or about 10 to 50 µg/kg of body weight The route of administration, which is preferred according to the invention, is administration by subcutaneous route. Intramuscular administration is further preferred according to the invention.

In further preferred embodiments, the IL-18BP isoform in accordance with the invention is administered daily or every other day.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, the IL-18BP isoform in accordance with the invention can be administered prophylactically or therapeutically to an individual prior to, simultaneously or sequentially with other therapeutic regimens or agents (e.g. multiple drug regimens), in a therapeutically effective amount, in particular with an interferon. Active agents that are administered simultaneously with other therapeutic agents can be administered in the same or different compositions.

The invention further relates to a method for treating an neurological and/or inflammatory disease comprising administering to a patient in need thereof an effective amount of an IL-18BP isoform in accordance with the invention, or of an agonist thereof, optionally together with a pharmaceutically acceptable carrier.

In such a method, the IL-18BP isoform or agonist thereof may be administered together with a polypeptide selected from the group consisting of an interferon, osteopontin and clusterin.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Having now described the invention, it will be more readily understood by reference to the following examples that are provided by way of illustration and are not intended to be limiting of the present invention.

EXAMPLES

Example 1

Recombinant Expression of IL-18BPb and d Isoforms

The IL-18BPb and IL-18BPd isoforms, fused to a tag at their C-terminal extremities to allow their purification, were expressed in HEK cells and purified as follows.

100 ml of culture medium sample containing the recombinant protein was diluted with 100 ml of cold buffer A (50 mM $NaH_2PO_4$; 600 mM NaCl; 8.7% (w/v) glycerol, pH 7.5). The sample was filtered through a 0.22 µm sterile filter (Millipore, 500 ml filter unit) and kept in a sterile square media bottle (Nalgene).

The purification was performed at 4° C. on a VISION workstation (Applied Biosystems) connected to an automatic sample loader (Labomatic). The purification procedure comprised two sequential steps: affinity chromatography specific for the tag followed by gel filtration on a Sephadex G-25 medium (Amersham Pharmacia) column (1.0×10 cm).

The first chromatography step resulted in the eluted protein collected in a 1.6 ml fraction.

For the second chromatography step, the Sephadex G-25 gel-filtration column was regenerated with 2 ml of buffer D (1.137 M NaCl; 2.7 mM KCl; 1.5 mM $KH_2PO_4$; 8 mM $Na_2HPO_4$; pH 7.2), and subsequently equilibrated with 4 column volumes of buffer C (137 mM NaCl; 2.7 mM KCl; 1.5 mM $KH_2PO_4$; 8 mM $Na_2HPO_4$; 20% (w/v) glycerol; pH 7.4). The peak fraction eluted from the first step was automatically loaded through the integrated sample loader of the VISION apparatus onto the Sephadex G-25 column. The protein was eluted with buffer C at a flow rate of 2 ml/min. The desalted sample was recovered in a 2.2 ml fraction. The fraction was filtered through a 0.22 µm sterile centrifugation filter (Millipore), frozen and stored at −80° C. An aliquot of the sample was analyzed on SDS-PAGE (4-12% NuPAGE gel; Novex) by coomassie staining and Western blot with anti-tag antibodies.

Coomassie staining: the NuPAGE gel was stained in a 0.1% coomassie blue R250 staining solution (30% methanol, 10% acetic acid) at room temperature for 1 hour, and subsequently destained in a 20% methanol, 7.5% acetic acid solution until the background was clear and the protein bands clearly visible.

Western blot: following an electrophoresis, the proteins were electrotransferred from the gel to a nitrocellulose membrane at 290 mA for 1 hour at 4° C. The membrane was blocked with 5% milk powder in buffer E (137 mM NaCl; 2.7 mM KCl; 1.5 mM $KH_2PO_4$; 8 mM $Na_2HPO_4$; 0.1% Tween 20, pH 7.4) for 1 h at room temperature. The membrane was subsequently incubated overnight at 4° C. with a mixture of 2 rabbit polyclonal anti-tag antibodies (G-18 and H-15, 0.2 ug/ml each; Santa Cruz) in buffer E comprising 2.5% milk powder. After a supplementary hour of incubation at room temperature, the membrane was washed with buffer E (3×10 min), and incubated for 2 hours at room temperature with a secondary HRP-conjugated anti-rabbit antibody (DAKO, HRP 0399) diluted at 1/3000, in buffer E containing 2.5% milk powder. After washing with buffer E (3×10 minutes), the membrane was developed with the ECL kit (Amersham Pharmacia) for 1 min. The membrane was subsequently exposed to a Hyperfilm (Amersham Pharmacia), the film developed, and the western blot image visually analyzed.

Protein assay: the protein concentration was determined using the BCA protein assay kit (Pierce) with bovine serum albumin as standard. The average protein recovery was 216 µg purified IL-18 bp per 500 ml culture medium.

Example 2

Effect of the IL-18BPb and IL-18BPd Isoforms on STAT2 Nuclear Translocation in Human Glioblastoma Cells U373

Abbreviations:
STAT: Signal transducer and activator of transcription.
U373: Glioblastoma cells from human origin.
ArrayScan HCS System (from Cellomics™): Image analysis system.
Nuclear translocation units: Nuclear translocation was measured using the "Cytoplasm to Nucleus Translocation Application" software (Image analysis system, ArrayScan HCS System, Cellomics™) Nuclear translocation units represent the measurement of the average intensity of the target in the nuclear region, minus the average intensity of the cytoplasm region. The nuclear translocation units are an average value for all analyzed cells in a given well (approximately 100 cells/well). In the software that was used, the function name is "MeanNuc-CytoIntenDiff" and the units are "intensity of fluorescence".
s.e.m.: standard error of the mean
Introduction The effect of IL-18BPb and IL-18BPd on astrocyte biology was evaluated. A series of assays based on the translocation from the cytoplasm to the nucleus of transcription factors such as c-Jun, NFκB, STAT1, STAT2 and STAT3, was performed on the human astroglioma cell line U373. The positive controls were: IL-1 for c-Jun and NFκB assays, IFNγ for STAT1 and STAT3 assays, and IFNβ for STAT2 assay.

Materials and Methods

U373 cells (ECACC, ref no: 89081403) were seeded at a density of 4000 cells/well in 96-well-plates (Packard View-Plate™-96, black, catalogue No. 6005225) in 80 µl of DMEM containing 10% FCS. The plates were left overnight at 37° C. in a humidified 5% $CO_2$ incubator. The day after, 20 µl of culture medium containing the protein to bed tested was added to the wells. Thirty minutes later, the medium was removed, and the cells were fixed with 3.7% formaldehyde (Sigma, catalogue No. 25, 254-9).

The cells were processed for immunostaining using commercial kits and according to the manufacturer's instruction. For the c-Jun assay, the Cellomics c-Jun activation HitKit™ (catalogue No. K01-0003-1) was used. For the NFκB assay, the Cellomics NFκB activation HitKit™ (catalogue No. K01-0001-1) was used. For the STAT1 assay, the Cellomics STAT1 activation HitKit™ (catalogue No. K01-0002-1) was used. For the STAT2 assay, the Cellomics STAT2 activation HitKit™ (catalogue No. K01-0005-1) was used. For the STAT3 assay, the Cellomics STAT3 activation HitKit™ (catalogue No. K01-0008-1) was used.

After immunostaining, the plates were read on an Array-Scan II apparatus.

Positive controls: for the c-Jun and NFκB nuclear translocation assays, 0.5 ng/ml of IL-1β (R&D systems, catalogue No. 201-LB) was used as a positive control. For the STAT2 nuclear translocation assay, 1000 IU/ml of recombinant human IFNβ was used as a positive control. For the STAT1 and STAT3 assays, 5000 IU/ml of recombinant human IFNγ (R&D systems, catalogue No. 285-IF-100) was used as a positive control.

Data Analysis

Results were expressed as nuclear translocation units. In order to compare several experiments, results were also expressed as a percentage of the maximal stimulation calculated with the positive controls (IL-1β, IFNγ and IFNβ). Statistics were performed using Student's T test or analysis of variance (ANOVA) and one-way ANOVA, followed by Dunnett's test depending of the number of groups per experiments. The threshold of significance was set at $p < 0.05$. The results were expressed as mean±standard error of the mean (s.e.m.).

Results

Figure 3B:
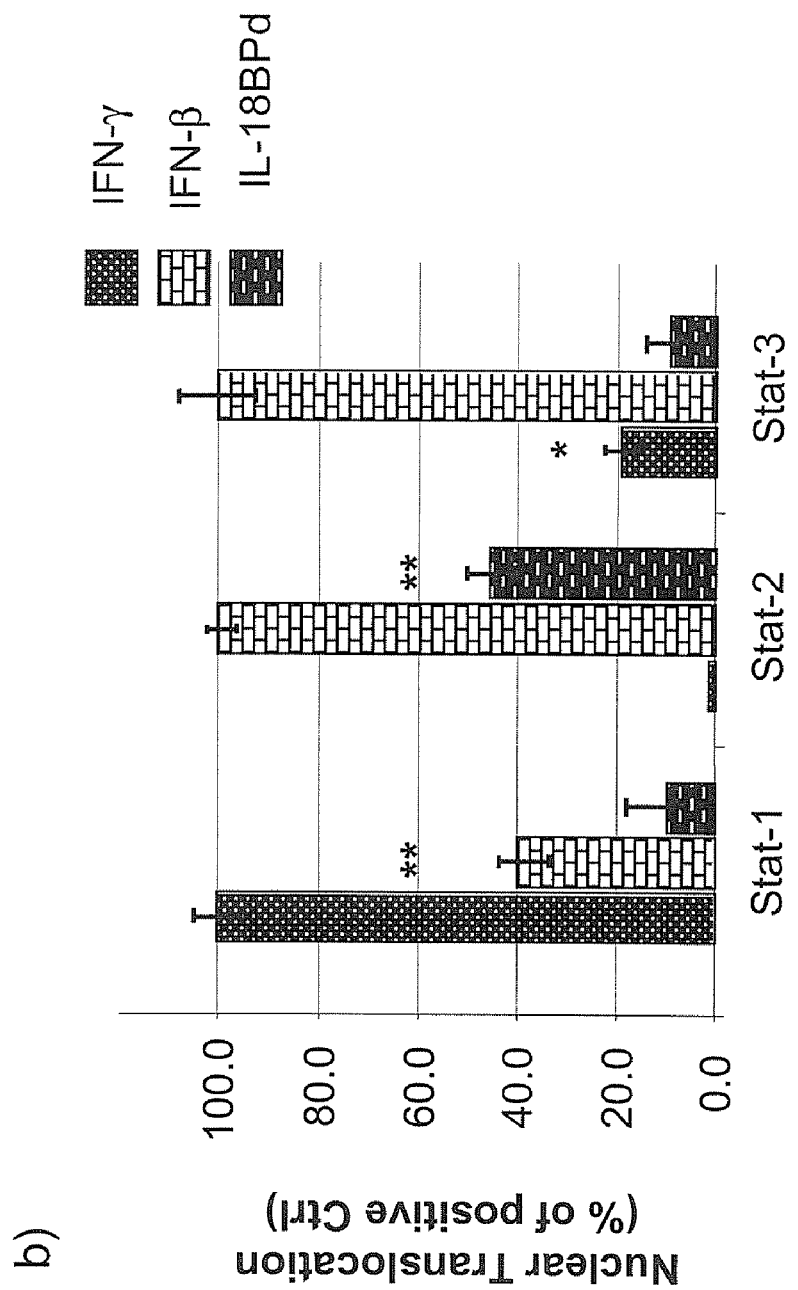
FIG. 3B shows the effect of IL-18BPd on STAT1, STAT2 and STAT3 nuclear translocation. The controls are: translocation induced by IFNγ for STAT1, and translocation induced by IFNβ for STAT2 and STAT3. Significance was calculated versus non-stimulated cells, *p<0.01, **p<0.001.

Adding IL-18BPb or IL-18BPd to U373 cells significantly stimulated STAT2 nuclear translocation (FIG. 3a). The stimulation corresponded to 30-50% of the maximal stimulation achieved with IFNβ. IL-18BPb and IL-18BPd did not induce STAT1, STAT3, c-Jun or NFκB nuclear translocation (FIG. 3b for results obtained with STAT1 and STAT3).

Figure 4:
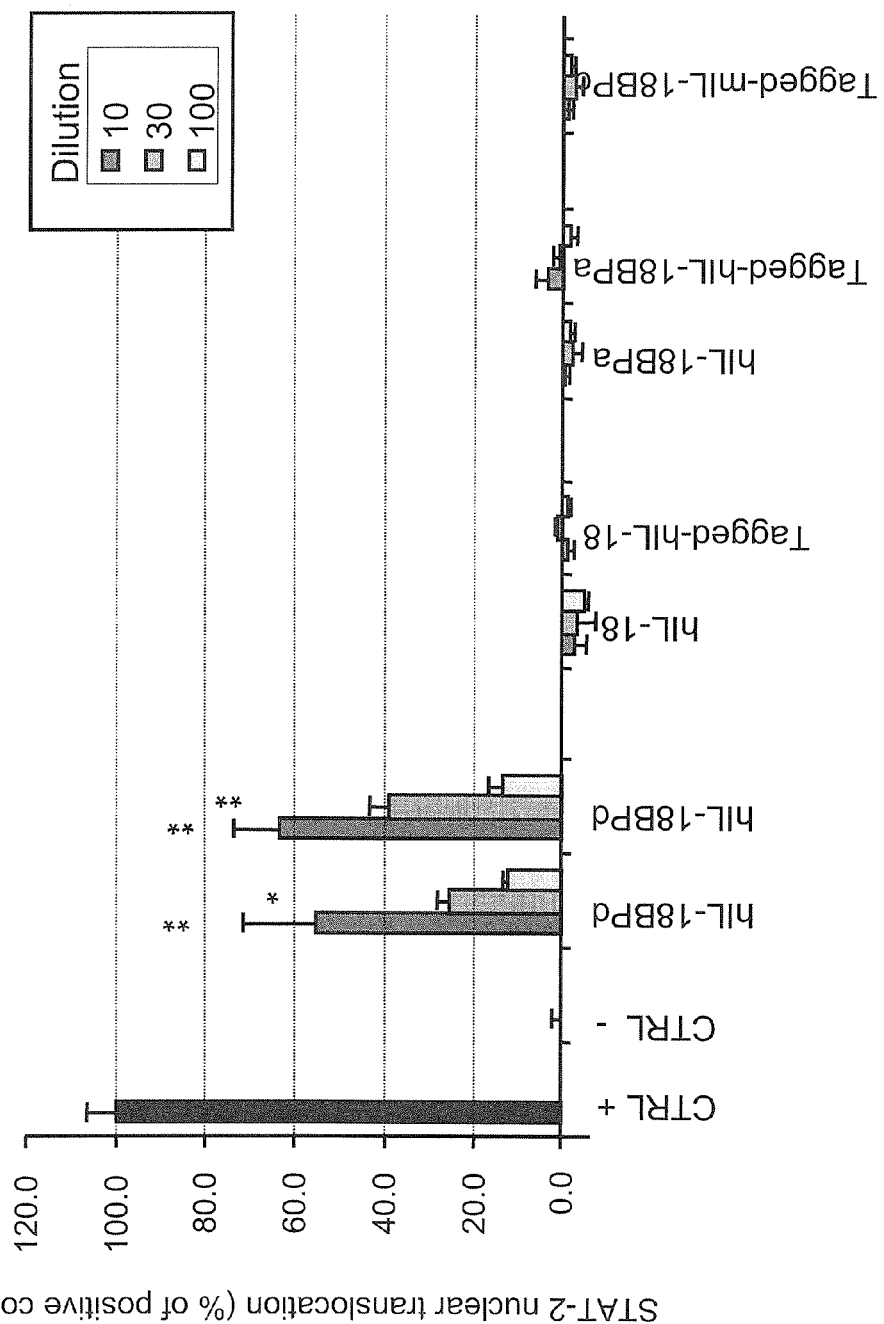
FIG. 4 shows the effect of IL-18 and IL-18BPa on STAT2 nuclear translocation in U373 cells. The positive control is translocation induced by IFN. Significance was calculated versus non-stimulated wells, *p<0.01, **p<0.001.

Recombinant human IL-18BPa, recombinant human IL-18BPc and recombinant mouse IL-18BPd (the ortholog of human IL-18BPa) were also tested on STAT2 nuclear translocation in U373. None of these IL-18BP isoforms and variants stimulated STAT2 translocation (FIG. 4 for results obtained with IL-18BPa and mIL-18BPd).

IL-18, the natural ligand for IL-18BPa and IL-18BPc, did not induce STAT2 translocation either (FIG. 4), highlighting the fact that the effect obtained with IL-18BPb and d is not a common effect to all IL-18BP isoforms.

Conclusions

The experiments above show that IL-18BPb and IL-18BPd have the capacity to initiate intracellular signaling by inducing STAT2 nuclear translocation in U373 cells. The induction of STAT2 nuclear translocation is specific since other transcription factors such as c-Jun, NFκB, STAT1 and STAT3 are not induced. The fact that IL-18BPa and IL-18BPc are not stimulating STAT2 translocation, together with the amino-acid sequence comparison between all isoforms (FIG. 2), suggests that the 36 carboxy-terminal amino-acid of IL-18BPb and IL-18BPd mediate the specificity of the response. These 36 carboxy-terminal amino-acid of IL-18BPb and IL-18BPd correspond to amino acids 78 to 113 of SEQ ID NO: 2.

Example 3

IL-18BPb & d attenuate IL-6 and MCP-1 production in human glioblastoma cells U373 and U251

Introduction

IL-6 and MCP-1 are pro-inflammatory chemokines. IL-1β and IFNγ stimulate IL-6 and MCP-1 secretion in human glioblastoma cells U373 and U251. The effect of IL-18BPb and IL-18BPd on IL-6 and on MCP-1 secretion in U373 or U251 cells stimulated by IL-1β and IFNγ was tested.

Materials and Methods

U373 cells (ECACC, ref no: 89081403) or U251 cells (Health Science Research Resources Bank (HSRRB) ref: U-251 MG) were seeded at a density of 4000 cells/well in 96-well-plates (Packard ViewPlate™-96, black, cat. 6005225) in 100 μl of DMEM containing 10% FCS. The cells were left overnight at 37° C. in a humidified 5% $CO_2$ incubator. The day after, 20 μl of culture medium containing the protein to be tested was added to the wells together with 80 μl of medium containing IL-1β and IFNγ. The final concentrations of IL-1β and IFNγ were the following: 0, 1, 3, 10 and 30 μg/ml. Twenty-four and 48 hours later, 50 μl of medium was harvested. IL-6 and MCP-1 levels were measured using ELISA kits (R&D systems: Duoset Human IL-6, catalogue No. DY206; Duoset Human MCP-1, catalogue No. DY279).

Data Analysis

Results were expressed as pg of protein per ml. Statistics were performed using Student's T test or analysis of variance (ANOVA) and one-way ANOVA, followed by Dunnett's test depending of the number of groups per experiments. The significance threshold was set at $p<0.05$. The results were expressed as mean±standard error of the mean (s.e.m.).

Results

Figure 5B:
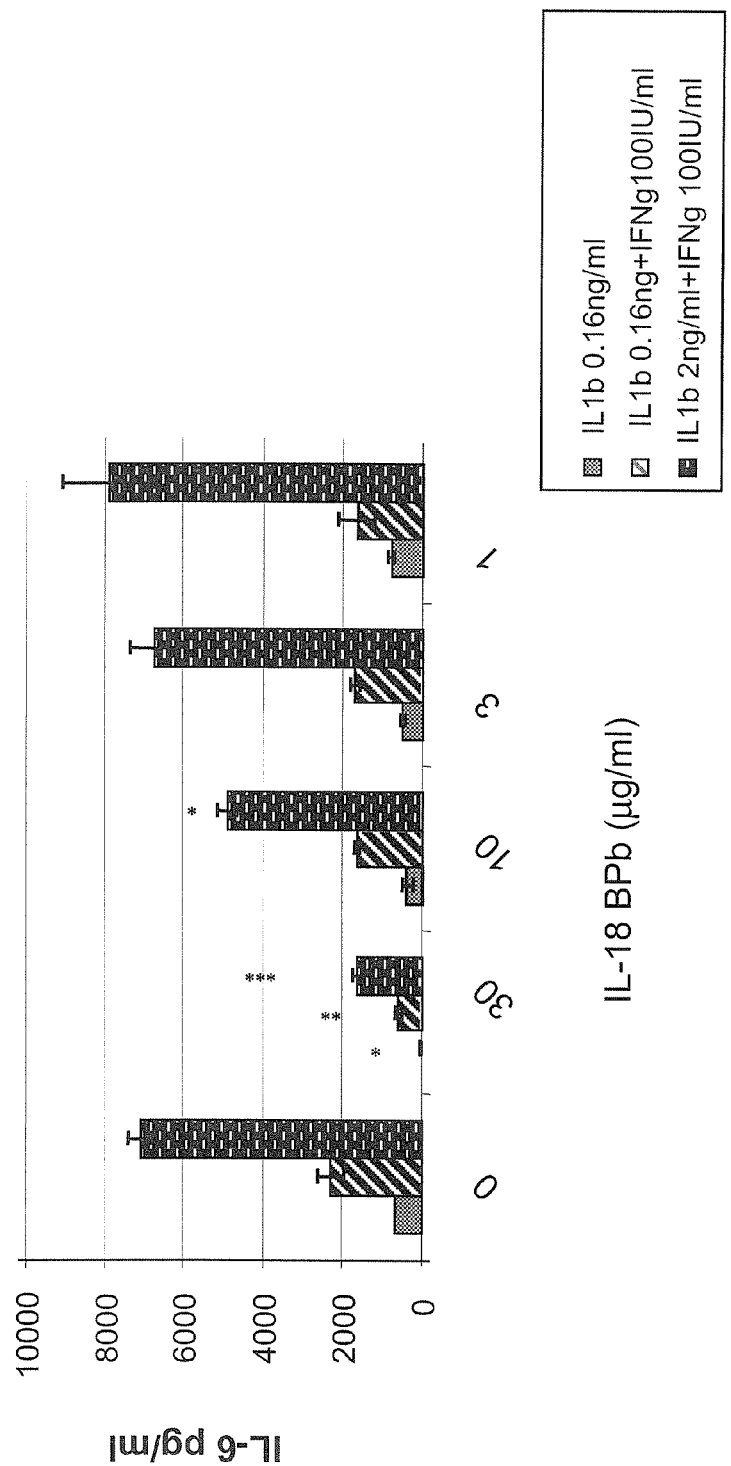
FIG. 5B shows the effect of IL-18BPb on IL-6 secretion by U251 cells stimulated by IL-1β and IFNγ, 24 hrs after stimulation. Significance was calculated versus stimulated cells not treated with IL-18BPb, *p<0.01 p<0.005, *p<0.001.

Treating U373 cells with IL-1β induced both IL-6 and MCP-1 secretion in a dose dependent manner. Supplemental addition of IFNγ further increases both IL-6 and MCP-1 secretion (FIG. 5a). Treating the cells with IL-18BPb or IL-18BPd concomitantly to IL-1β+/−IFNγ significantly decreased the level of IL-6 secretion and of MCP-1 secretion (FIG. 5a) in a dose dependent manner. The same effect was obtained with another human astroglial cell lines, U251 (FIG. 5b). It was also shown that IL-18BPb alone or IL-18BPd alone did not induce IL6 or MCP-1 secretion by U251 or U373 cells.

Conclusions

These series of experiments demonstrate the anti-inflammatory function of IL-18BPb and of IL-18BPd in a model of IL-1β and IFNγ induced response.

Example 4

IL-18BPb and IL-18BPd Protect Against TRAIL Induced Apoptosis

Introduction

The ability of IL-18BPb and IL-18BPd to rescue cells from TRAIL induced apoptosis was investigated in L929 cells, a murine fibroblast cell line.

Materials and Methods

L929 mouse fibroblast cells (CCL-1) were seeded in 96 wells-plates at 20,000 cells/well in 100 μl of DMEM containing 2% FCS. The cells were incubated overnight at 37° C. in a 5% $CO_2$ humidified chamber. The day after, the medium was replaced by fresh medium containing 1 μg/ml of actinomycin D (Fluka ref 01817) and 2 ng/ml of TRAIL (R&D, recombinant human Trail/TNFS10 Cat# 375-TEC) in order to induce apoptosis. Twenty-four hours later, LDH levels in supernatant were determined (Promega ref: G179A). 10 ng/ml of Osteoprotegerin (R&D cat#:185-OS) was used as a positive control.

Data Analysis

Results were expressed as optical density (OD). Statistics were performed using measure analysis of variance (ANOVA) and one-way ANOVA, followed by Dunnett's test. The level of significance was set at $p<0.05$. The results were expressed as mean±standard error of the mean (s.e.m.).

Results

Figure 6:
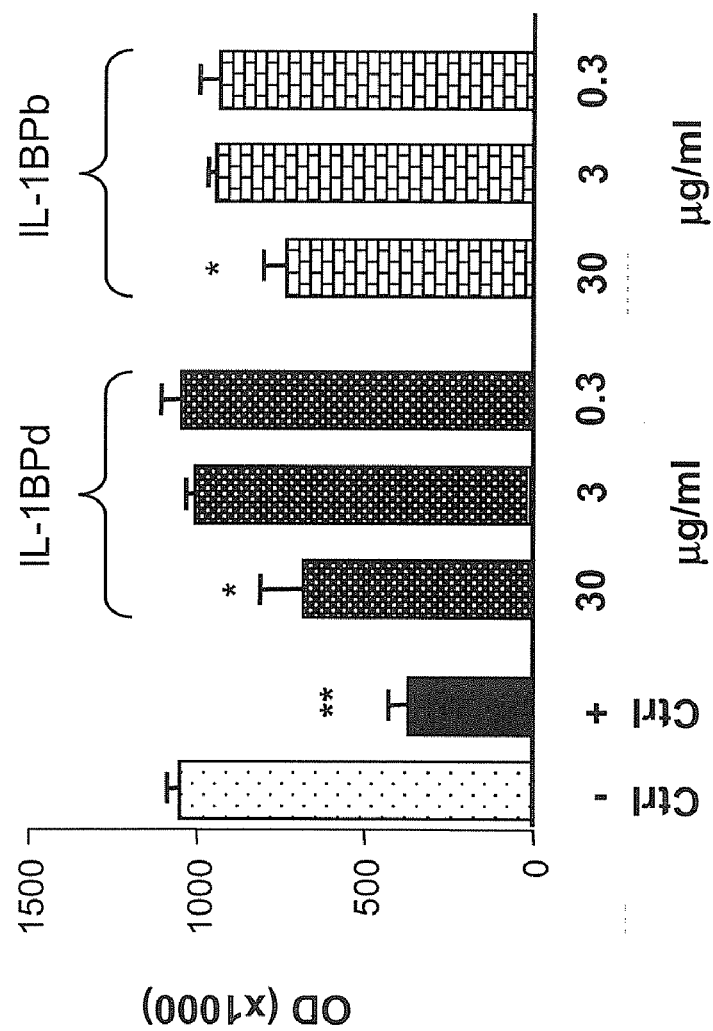
FIG. 6 shows the effect of IL-18BPb & IL-18BPd on Trail-induced apoptosis on L929 cells. Significance was calculated versus TRAIL stimulated cells, *p<0.05**p<0.005.

Adding IL-18BPb or d to the culture medium significantly protected L929 cells from Trail-induced apoptosis. The protection level obtained with 30 μg/ml of IL-18BPb was equal to 47% of the protection level obtained with Osteoprotegerin, and the protection level obtained with 30 μg/ml of IL-18BPd was equal to 55% of the protection level obtained with Osteoprotegerin (FIG. 6).

Conclusion

These experiments reveal the protective role of IL-18BPb and IL-18BPd in an apoptosis mediated cell death assay. Thus IL-18BPb and IL-18BPd exhibit an anti-apoptotic activity on fibroblasts.

Example 5

Tissue Expression of the IL-18BPd Isoform

Introduction

A real-time PCR analysis for the expression of IL-18BPd was performed on various human tissues in order to provide information on its tissue distribution.

Materials and Methods

The primers of SEQ ID Nos. 7-12 were designed using Primer Express software from PE Applied Biosystems (Foster City, Calif.). SEQ ID Nos. 5 and 6 correspond to GAPDH specific primers (housekeeping control). SEQ ID Nos. 7 and 8 correspond to intron-GAPDH primers (DNA contamination control). SEQ ID Nos. 9 and 10 correspond to primers amplifying all human IL-18BP isoforms. SEQ ID Nos. 11 and 12 correspond to primers specific for the hIL-18BPd isoform.

Potential genomic DNA contamination was excluded by performing PCR with specific intron-GAPDH primers. The absence of nonspecific amplification was confirmed by analyzing the PCR products by agarose gel electrophoresis. Real-time PCR was performed with 5 µl/well of reverse transcription products (0.5 ng total RNA), 25 µl/well SYBR Green PCR master mix (PE Applied Biosystems) with 0.5 U/well of AmpErase uracil N-glycosylase and 300 nM primers. PCR was performed at 50° C. for 2 min and 95° C. for 10 min, and then run for 40 cycles at 95° C. for 15 and 60° C. for 1 min on the ABI PRISM 7700 Detection System (PE Applied Biosystems). The tissue reverse transcribed cDNA samples were thus amplified and their cycle threshold values were determined. All cycle threshold values were normalized to the housekeeping gene GAPDH.

Figure 7:
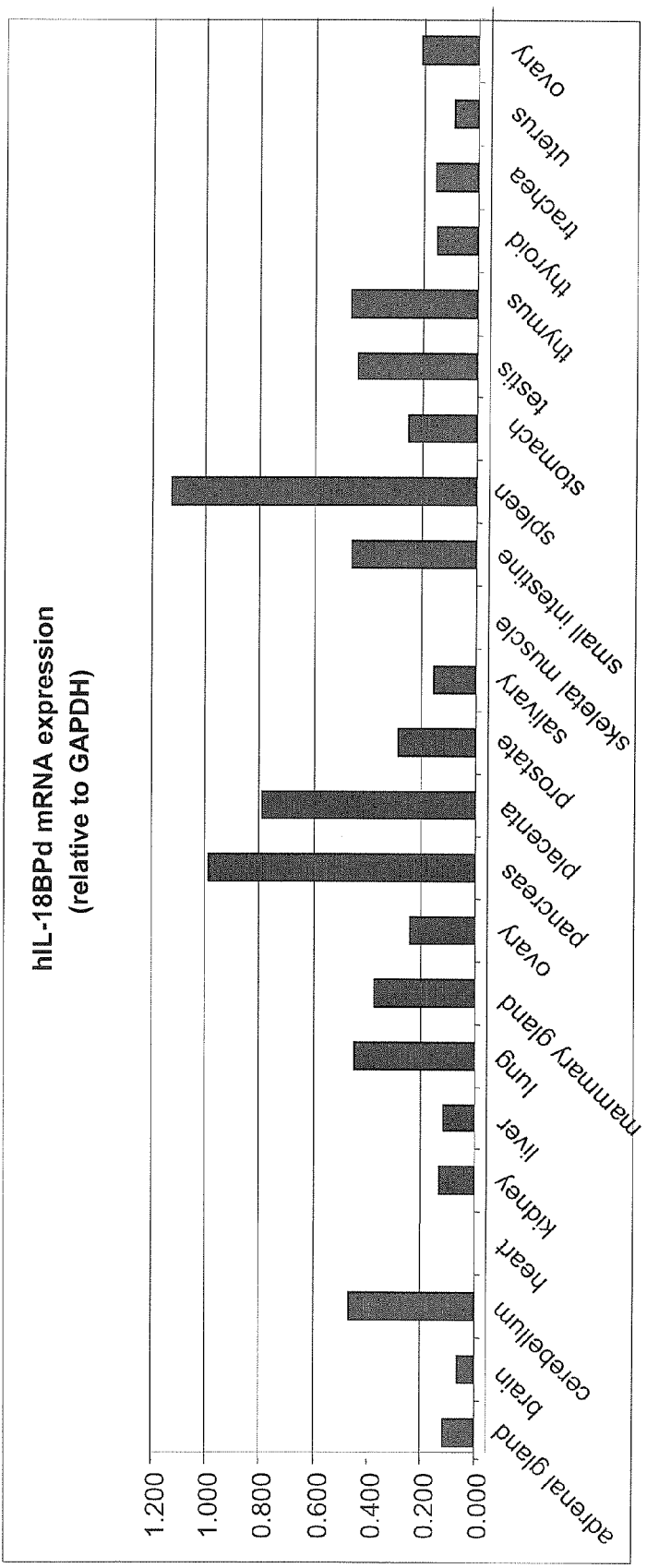
FIG. 7 shows expression of IL-18BPd in various human tissues. GAPDH expression was used as an internal control.

Results:

The Taqman analysis revealed substantial differences in the tissue distribution of IL-18BPd. IL-18BPd was predominantly expressed in spleen, pancreas and placenta (80% or more of GAPDH expression) (FIG. 7).

When using primers amplifying the mRNAs of all four IL-18BP isoforms, transcripts were detected in heart and muscles (result not shown). Interestingly, heart and muscles were devoid of IL-18BPd mRNA (FIG. 7). The IL-18BP transcripts detected in these organs probably correspond to mRNAs of isoform IL-18BPa, which had previously been shown to be expressed in these organs (Mallat et al., 2004).

Conclusion:

These results suggest an organ-dependent regulation of IL-18BPd expression. In addition, they confirm the fact that IL-18BPd expression is not a side product of IL-18BPa.

In conclusion, the IL-18BPd isoform exhibits both its own mechanisms of action and its own expression pattern.

REFERENCES

1. Altschul, S. F., Gish, W., Miller, W., Myers, E. W., and Lipman, D. J. (1990). Basic local alignment search tool. J. Mol. Biol. 215, 403-410.
2. Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic Acids Res. 25, 3389-3402.
3. Brutlag, D. L., Dautricourt, J. P., Maulik, S., and Relph, J. (1990). Improved sensitivity of biological sequence database searches. Comput. Appl. Biosci. 6, 237-245.
4. Chater, K. F. Sixth International Symposium on Actinomycetales Biology. 45-54. 1986. Akademiai Kaido, Budapest, Hungary.
5. Comabella, M., Imitola, J., Weiner, H. L., and Khoury, S. J. (2002). Interferon-beta treatment alters peripheral blood monocytes chemokine production in MS patients. J. Neuroimmunol. 126, 205-212.
6. Consilvio, C., Vincent, A. M., and Feldman, E. L. (2004). Neuroinflammation, COX-2, and ALS—a dual role? Exp. Neurol. 187, 1-10.
7. Conti, B., Jahng, J. W., Tinti, C., Son, J. H., and Joh, T. H. (1997). Induction of interferon-gamma inducing factor in the adrenal cortex. J. Biol. Chem. 272, 2035-2037.
8. Conti, P. and DiGioacchino, M. (2001). MCP-1 and RANTES are mediators of acute and chronic inflammation. Allergy Asthma Proc. 22, 133-137.
9. DiDonato, J. A., Hayakawa, M., Rothwarf, D. M., Zandi, E., and Karin, M. (1997). A cytokine-responsive IkappaB kinase that activates the transcription factor NF-kappaB. Nature 388, 548-554.
10. Eikelenboom, P., Bate, C., Van Gool, W. A., Hoozemans, J. J., Rozemuller, J. M., Veerhuis, R., and Williams, A. (2002). Neuroinflammation in Alzheimer's disease and prion disease. Glia 40, 232-239.
11. Gao, H. M., Liu, B., Zhang, W., and Hong, J. S. (2003). Novel anti-inflammatory therapy for Parkinson's disease. Trends Pharmacol. Sci. 24, 395-401.
12. Gonnet, G. H., Cohen, M. A., and Benner, S. A. (1992). Exhaustive matching of the entire protein sequence database. Science 256, 1443-1445.
13. Grantham, R. (1974). Amino acid difference formula to help explain protein evolution. Science 185, 862-864.
14. Henikoff, S, and Henikoff, J. G. (1993). Performance evaluation of amino acid substitution matrices. Proteins 17, 49-61.
15. Higgins, D. G., Thompson, J. D., and Gibson, T. J. (1996). Using CLUSTAL for multiple sequence alignments. Methods Enzymol. 266, 383-402.
16. Hua, L. L., Kim, M. O., Brosnan, C. F., and Lee, S. C. (2002). Modulation of astrocyte inducible nitric oxide synthase and cytokine expression by interferon beta is associated with induction and inhibition of interferon gamma-activated sequence binding activity. J. Neurochem. 83, 1120-1128.
17. Hunter, C. L., Bachman, D., and Granholm, A. C. (2004). Minocycline prevents cholinergic loss in a mouse model of Down's syndrome. Ann. Neurol. 56, 675-688.
18. Infante, J., Llorca, J., Berciano, J., and Combarros, O. (2005). Interleukin-8, intercellular adhesion molecule-1 and tumour necrosis factor-alpha gene polymorphisms and the risk for multiple system atrophy. J. Neurol. Sci. 228, 11-13.
19. Karlin, S, and Altschul, S. F. (1990). Methods for assessing the statistical significance of molecular sequence features by using general scoring schemes. Proc. Natl. Acad. Sci. U.S.A 87, 2264-2268.
20. Kim, S. H., Eisenstein, M., Reznikov, L., Fantuzzi, G., Novick, D., Rubinstein, M., and Dinarello, C. A. (2000). Structural requirements of six naturally occurring isoforms of the IL-18 binding protein to inhibit IL-18. Proc. Natl. Acad. Sci. U.S.A 97, 1190-1195.
21. Maliszewski, C. R., Sato, T. A., Vanden Bos, T., Waugh, S., Dower, S. K., Slack, J., Beckmann, M. P., and Grabstein, K. H. (1990). Cytokine receptors and B cell func- 21. Recombinant soluble receptors specifically inhibit IL-1- and IL-4-induced B cell activities in vitro. J. Immunol. 144, 3028-3033.
22. Mallat, Z., Heymes, C., Corbaz, A., Logeart, D., Alouani, S., Cohen-Solal, A., Seidler, T., Hasenfuss, G., Chvatchko, Y., Shah, A. M., and Tedgui, A. (2004). Evidence for altered interleukin 18 (IL)-18 pathway in human heart failure. FASEB J. 18, 1752-1754.
23. Micallef, M. J., Ohtsuki, T., Kohno, K., Tanabe, F., Ushio, S., Namba, M., Tanimoto, T., Torigoe, K., Fujii, M., Ikeda, M., Fukuda, S., and Kurimoto, M. (1996). Interferon-gamma-inducing factor enhances T helper 1 cytokine production by stimulated human T cells: synergism with interleukin-12 for interferon-gamma production. Eur. J. Immunol. 26, 1647-1651.
24. Nakamura, K., Okamura, H., Wada, M., Nagata, K., and Tamura, T. (1989). Endotoxin-induced serum factor that stimulates gamma interferon production. Infect. Immun. 57, 590-595.
25. Noseworthy, J. H. (1999). Progress in determining the causes and treatment of multiple sclerosis. Nature 399, A40-A47.
26. Novick, D., Kim, S. H., Fantuzzi, G., Reznikov, L. L., Dinarello, C. A., and Rubinstein, M. (1999). Interleukin-18 binding protein: a novel modulator of the Th1 cytokine response. Immunity. 10, 127-136.
27. Panenka, W., Jijon, H., Herx, L. M., Armstrong, J. N., Feighan, D., Wei, T., Yong, V. W., Ransohoff, R. M., and MacVicar, B. A. (2001). P2X7-like receptor activation in astrocytes increases chemokine monocyte chemoattractant protein-1 expression via mitogen-activated protein kinase. J. Neurosci. 21, 7135-7142.
28. Parnet, P., Garka, K. E., Bonnert, T. P., Dower, S. K., and Sims, J. E. (1996). IL-1 Rrp is a novel receptor-like molecule similar to the type I interleukin-1 receptor and its homologues T1/ST2 and IL-1R AcP. J. Biol. Chem. 271, 3967-3970.
29. Pearson, W. R. and Lipman, D. J. (1988). Improved tools for biological sequence comparison. Proc. Natl. Acad. Sci. U.S. A 85, 2444-2448.
30. Perry, V. H. (2004). The influence of systemic inflammation on inflammation in the brain: implications for chronic neurodegenerative disease. Brain Behav. Immun. 18, 407-413.
31. Pfitzner, E., Kliem, S., Baus, D., and Litterst, C. M. (2004). The role of STATs in inflammation and inflammatory diseases. Curr. Pharm. Des 10, 2839-2850.
32. Rothe, H., Jenkins, N. A., Copeland, N. G., and Kolb, H. (1997). Active stage of autoimmune diabetes is associated with the expression of a novel cytokine, IGIF, which is located near Idd2. J. Clin. Invest 99, 469-474.
33. Stoll, G., Jander, S., and Myers, R. R. (2002). Degeneration and regeneration of the peripheral nervous system: from Augustus Waller's observations to neuroinflammation. J. Peripher. Nerv. Syst. 7, 13-27.
34. Thompson, J. D., Higgins, D. G., and Gibson, T. J. (1994). CLUSTAL W: improving the sensitivity of progressive multiple sequence alignment through sequence weighting, position-specific gap penalties and weight matrix choice. Nucleic Acids Res. 22, 4673-4680.
35. Tuppo, E. E. and Arias, H. R. (2005). The role of inflammation in Alzheimer's disease. Int. J. Biochem. Cell Biol. 37, 289-305.
36. Ushio, S., Namba, M., Okura, T., Hattori, K., Nukada, Y., Akita, K., Tanabe, F., Konishi, K., Micallef, M., Fujii, M., Torigoe, K., Tanimoto, T., Fukuda, S., Ikeda, M., Okamura, H., and Kurimoto, M. (1996). Cloning of the cDNA for human IFN-gamma-inducing factor, expression in *Escherichia coli*, and studies on the biologic activities of the protein. J. Immunol. 156, 4274-4279.
37. Yan, R., Qureshi, S., Zhong, Z., Wen, Z., and Darnell, J. E., Jr. (1995). The genomic structure of the STAT genes: multiple exons in coincident sites in Stat1 and Stat2. Nucleic Acids Res. 23, 459-463.
38. Yoshimoto, T., Takeda, K., Tanaka, T., Ohkusu, K., Kashiwamura, S., Okamura, H., Akira, S., and Nakanishi, K. (1998). IL-12 up-regulates IL-18 receptor expression on T cells, Th1 cells, and B cells: synergism with IL-18 for IFN-gamma production. J. Immunol. 161, 3400-3407.

The invention claimed is:

1. A method of treating acute disseminated encephalomyelitis (ADEM), chronic inflammatory demyelinating polyradiculoneuropathy (CIDP), Guillain-Barré syndrome (GBS), peripheral neuropathy, traumatic nerve injury, traumatic brain injury or amyotrophic lateral sclerosis (ALS) comprising administering a composition comprising an IL-18 binding protein (IL-18BP) isoform to an individual having a disease selected from acute disseminated encephalomyelitis (ADEM), chronic inflammatory demyelinating polyradiculoneuropathy (CIDP), Guillain-Barré syndrome (GBS), peripheral neuropathy, traumatic nerve injury, traumatic brain injury or amyotrophic lateral sclerosis (ALS), wherein said composition is administered in an amount effective to treat said disease and said IL-18BP isoform is selected from the group consisting of:
   (a) polypeptide comprising amino acids 1 to 113 of SEQ ID NO: 1;
   (b) a polypeptide comprising amino acids 29 to 113 of SEQ ID NO: 1;
   (c) a polypeptide comprising amino acids 78 to 113 of SEQ ID NO: 1;
   (d) a polypeptide comprising amino acids 1 to 161 of SEQ ID NO: 2;
   (e) a polypeptide comprising amino acids 29 to 161 of SEQ ID NO: 2; and
   (f) a fusion protein comprising a polypeptide according to any one of (a)-(e).

2. The method according to claim 1, wherein said IL-18BP isoform is fused to a carrier molecule, a peptide or a protein that promotes the crossing of the blood brain barrier.

3. The method according to claim 1, wherein said IL-18BP isoform is PEGylated.

4. The method according to claim 2, wherein said IL-18BP isoform is fused to an immunoglobulin (Ig) domain.

5. The method according to claim 1, wherein said method further comprises the administration of a composition comprising a polypeptide selected from the group consisting of an interferon, osteopontin and clusterin.

6. The method according to claim 1, wherein said IL-18BP isoform is administered in an amount of about 0.001 to 100 mg/kg of body weight.

7. The method according to claim 1, wherein said IL-18BP isoform is administered in an amount of about 0.01 to 10 mg/kg of body weight.

8. The method according to claim 1, wherein said IL-18BP isoform is administered in an amount of about 9, 8, 7, 6, 5, 4, 3, 2 or 1 mg/kg of body weight.

9. The method according to claim 1, wherein said IL-18BP isoform is administered in an amount of about 0.1 to 1 mg/kg of body weight.

10. The method according to claim 1, wherein said IL-18BP isoform is a polypeptide comprising amino acids 1 to 113 of SEQ ID NO: 1.

11. The method according to claim 1, wherein said IL-18BP isoform is a polypeptide comprising amino acids 29 to 113 of SEQ ID NO: 1.

12. The method according to claim 1, wherein said IL-18BP isoform is a polypeptide comprising amino acids 78 to 113 of SEQ ID NO: 1.

13. The method according to claim 1, wherein said IL-18BP isoform is a polypeptide comprising amino acids 1 to 161 of SEQ ID NO: 2.

14. The method according to claim 1, wherein said IL-18BP isoform is a polypeptide comprising amino acids 29 to 161 of SEQ ID NO: 2.

15. The method according to claim 2, wherein said IL-18BP isoform is fused to a carrier molecule through a peptide linker comprising Glu-Phe-Met or Glu-Phe-Gly-Ala-Gly-Leu-Val-Leu-Gly-Gly-Gln-Phe-Met (SEQ ID NO: 13).

16. The method according to claim 1, wherein said disease is acute disseminated encephalomyelitis (ADEM).

17. The method according to claim 1, wherein said disease is chronic inflammatory demyelinating polyradiculoneuropathy (CIDP).

18. The method according to claim 1, wherein said disease is Guillain-Barré syndrome (GBS).

19. The method according to claim 1, wherein said disease is traumatic nerve injury.

20. The method according to claim 1, wherein said disease is peripheral neuropathy.

21. The method according to claim 1, wherein said disease is traumatic brain injury.

22. The method according to claim 1, wherein said disease is amyotrophic lateral sclerosis (ALS).

23. The method according to claim 5, wherein said composition comprising a polypeptide selected from the group consisting of an interferon, osteopontin and clusterin is administered separately from a composition comprising an IL-18BP isoform.

24. The method according to claim 5, wherein said composition comprising a polypeptide selected from the group consisting of an interferon, osteopontin and clusterin is administered in combination with a composition comprising an IL-18BP isoform.

* * * * *

UNITED STATES PATENT AND TRADEMARK OFFICE
CERTIFICATE OF CORRECTION

| | |
|---|---|
| PATENT NO. | : 8,128,920 B2 |
| APPLICATION NO. | : 11/915913 |
| DATED | : March 6, 2012 |
| INVENTOR(S) | : Yves Sagot et al. |

It is certified that error appears in the above-identified patent and that said Letters Patent is hereby corrected as shown below:

Column 3,
Line 41, "genes in risk" should read --genes at risk--.

Column 11,
Lines 33-34, "found that that IL-18BPb" should read --found that IL-18BPb--.
Line 38, "IL-18α" should read --IL-18a--.

Column 12,
Lines 12-13, "in of Kim" should read --in Kim--.

Column 13,
Line 59, "including of destruction" should read --including destruction--.

Column 19,
Line 49, "corresponds to" should read --correspond to--.

Column 21,
Line 56, "neurologically disease" should read --neurological disease--.

Column 22,
Lines 54-55, "neurologically diseases" should read --neurological diseases--.
Line 59, "neurologically diseases" should read --neurological diseases--.

Column 24,
Line 57, "meaning range" should read --mean range--.

Column 26,
Line 38, "IL-1 for" should read --IL-1β for--.

Signed and Sealed this
Twenty-ninth Day of May, 2012

David J. Kappos
*Director of the United States Patent and Trademark Office*

CERTIFICATE OF CORRECTION (continued)
U.S. Pat. No. 8,128,920 B2

Column 29,
Line 34, "for 15 and" should read --for 15 s and--.

SEQUENCE LISTING

```
<160> NUMBER OF SEQ ID NOS: 13

<210> SEQ ID NO 1
<211> LENGTH: 113
<212> TYPE: PRT
<213> ORGANISM: Homo sapiens
<220> FEATURE:
<221> NAME/KEY: SIGNAL
<222> LOCATION: (1)..(28)

<400> SEQUENCE: 1

Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
                20                  25                  30

Gln Thr Thr Thr Ala Ala Thr Ala Ser Val Arg Ser Thr Lys Asp Pro
            35                  40                  45

Cys Pro Ser Gln Pro Pro Val Phe Pro Ala Ala Lys Gln Cys Pro Ala
        50                  55                  60

Leu Glu Val Thr Trp Pro Glu Val Glu Val Pro Leu Ser Trp Ala Glu
65                  70                  75                  80
```

```
Gly Asn Leu Ala Pro His Pro Arg Ser Pro Ala Leu Gln Pro Gln Gln
            85                  90                  95

Ser Thr Ala Ala Gly Leu Arg Leu Ser Thr Gly Pro Ala Ala Ala Gln
            100                 105                 110

Pro

<210> SEQ ID NO 2
<211> LENGTH: 161
<212> TYPE: PRT
<213> ORGANISM: Homo sapiens
<220> FEATURE:
<221> NAME/KEY: SIGNAL
<222> LOCATION: (1)..(28)

<400> SEQUENCE: 2

Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
            20                  25                  30

Gln Thr Thr Thr Ala Ala Thr Ala Ser Val Arg Ser Thr Lys Asp Pro
            35                  40                  45

Cys Pro Ser Gln Pro Pro Val Phe Pro Ala Ala Lys Gln Cys Pro Ala
        50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
            85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Trp Ala Glu
            115                 120                 125

Gly Asn Leu Ala Pro His Pro Arg Ser Pro Ala Leu Gln Pro Gln Gln
            130                 135                 140

Ser Thr Ala Ala Gly Leu Arg Leu Ser Thr Gly Pro Ala Ala Ala Gln
145                 150                 155                 160

Pro

<210> SEQ ID NO 3
<211> LENGTH: 192
<212> TYPE: PRT
<213> ORGANISM: Homo sapiens
<220> FEATURE:
<221> NAME/KEY: SIGNAL
<222> LOCATION: (1)..(28)

<400> SEQUENCE: 3

Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
            20                  25                  30

Gln Thr Thr Thr Ala Ala Thr Ala Ser Val Arg Ser Thr Lys Asp Pro
            35                  40                  45

Cys Pro Ser Gln Pro Pro Val Phe Pro Ala Ala Lys Gln Cys Pro Ala
        50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
            85                  90                  95
```

```
Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Thr Gln Leu
            115                 120                 125

Cys Lys Ala Leu Val Leu Glu Gln Leu Thr Pro Ala Leu His Ser Thr
            130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
                165                 170                 175

Thr Gln Glu Ala Leu Pro Ser Ser His Ser Ser Pro Gln Gln Gln Gly
            180                 185                 190
```

<210> SEQ ID NO 4
<211> LENGTH: 197
<212> TYPE: PRT
<213> ORGANISM: Homo sapiens
<220> FEATURE:
<221> NAME/KEY: SIGNAL
<222> LOCATION: (1)..(28)

<400> SEQUENCE: 4

```
Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
            20                  25                  30

Gln Thr Thr Thr Ala Ala Thr Ala Ser Val Arg Ser Thr Lys Asp Pro
            35                  40                  45

Cys Pro Ser Gln Pro Pro Val Phe Pro Ala Ala Lys Gln Cys Pro Ala
50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Thr Gln Leu
            115                 120                 125

Cys Lys Ala Leu Val Leu Glu Gln Leu Thr Pro Ala Leu His Ser Thr
            130                 135                 140

Asn Phe Ser Cys Val Leu Val Asp Pro Glu Gln Val Val Gln Arg His
145                 150                 155                 160

Val Val Leu Ala Gln Leu Trp Val Arg Ser Pro Arg Arg Gly Leu Gln
                165                 170                 175

Glu Gln Glu Glu Leu Cys Phe His Met Trp Gly Lys Gly Gly Leu
            180                 185                 190

Cys Gln Ser Ser Leu
            195
```

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
gatgggattt ccattgatga ca                                      22

<210> SEQ ID NO 6
<211> LENGTH: 22
<212> TYPE: DNA
<213> ORGANISM: Artificial
<220> FEATURE:
<223> OTHER INFORMATION: primer

<400> SEQUENCE: 6
gatgggattt ccattgatga ca                                              22

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
cctagtccca gggctttgat t                                               21

<210> SEQ ID NO 8
<211> LENGTH: 22
<212> TYPE: DNA
<213> ORGANISM: Artificial
<220> FEATURE:
<223> OTHER INFORMATION: primer

<400> SEQUENCE: 8
ctgtgctccc actcctgatt tc                                              22

<210> SEQ ID NO 9
<211> LENGTH: 24
<212> TYPE: DNA
<213> ORGANISM: Artificial
<220> FEATURE:
<223> OTHER INFORMATION: primer

<400> SEQUENCE: 9
tcccatgtct ctgctcattt agtc                                            24

<210> SEQ ID NO 10
<211> LENGTH: 19
<212> TYPE: DNA
<213> ORGANISM: Artificial
<220> FEATURE:
<223> OTHER INFORMATION: primer

<400> SEQUENCE: 10
aaccaggctt gagcgttcc                                                  19

<210> SEQ ID NO 11
<211> LENGTH: 28
<212> TYPE: DNA
<213> ORGANISM: Artificial
<220> FEATURE:
<223> OTHER INFORMATION: primer

<400> SEQUENCE: 11
acgcagagac tgctactaca tcttattc                                        28

<210> SEQ ID NO 12
<211> LENGTH: 21
<212> TYPE: DNA
<213> ORGANISM: Artificial
<220> FEATURE:
<223> OTHER INFORMATION: primer

```
<400> SEQUENCE: 12
cccggtcctt aatttgttcc t                                        21

<210> SEQ ID NO 13
<211> LENGTH: 13
<212> TYPE: PRT
<213> ORGANISM: Artificial sequence
<220> FEATURE:
<223> OTHER INFORMATION: amino acid linker sequence

<400> SEQUENCE: 13

Glu Phe Gly Ala Gly Leu Val Leu Gly Gly Gln Phe Met
1               5                   10
```